United States Patent
Perumal et al.

(10) Patent No.: US 12,329,765 B2
(45) Date of Patent: Jun. 17, 2025

(54) TARGETED NANOPARTICLE FOR THE TREATMENT OF TRAUMATIC BRAIN INJURY AND OTHER CNS DISEASES

(71) Applicant: New Jersey Institute of Technology, Newark, NJ (US)

(72) Inventors: Venkatesan Perumal, Newark, NJ (US); Arun Reddy Ravula, Newark, NJ (US); Namas Chandra, Newark, NJ (US); Venkata Kakulavarapu RamaRao, Newark, NJ (US); Vivek Kumar, Newark, NJ (US); Zain Siddiqui, Paterson, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 126 days.

(21) Appl. No.: 17/730,358

(22) Filed: Apr. 27, 2022

(65) Prior Publication Data

US 2022/0347193 A1 Nov. 3, 2022

Related U.S. Application Data

(60) Provisional application No. 63/180,814, filed on Apr. 28, 2021.

(51) Int. Cl.
| | | |
|---|---|---|
| A61K 31/65 | (2006.01) | |
| A61K 9/16 | (2006.01) | |
| A61K 47/60 | (2017.01) | |
| A61K 47/64 | (2017.01) | |
| A61K 47/69 | (2017.01) | |
| A61P 25/28 | (2006.01) | |
| A61P 27/16 | (2006.01) | |

(52) U.S. Cl.
CPC ............ *A61K 31/65* (2013.01); *A61K 9/1658* (2013.01); *A61K 47/60* (2017.08); *A61K 47/644* (2017.08); *A61K 47/6929* (2017.08); *A61P 25/28* (2018.01); *A61P 27/16* (2018.01)

(58) Field of Classification Search
CPC ................................ A61P 25/28; A61K 31/65
See application file for complete search history.

(56) References Cited

U.S. PATENT DOCUMENTS 10,206,887 B2 * 2/2019 Desai .................... A61K 31/337

OTHER PUBLICATIONS

Mishra, V. et al., Targeted brain delivery of AZT via transferrin anchored pegylated albumin nanoparticles, Jan. 2006, J Drug Targeting, vol. 14, 45-53 (Year: 2006).*
Nagpal, K. et al., Evaluation of safety and efficacy of brain targeted chitosan nanoparticles of minocycline, Apr. 12, 2013, Int. J. Bio. Macro., vol. 59, 20-28 (Year: 2013).*
Saraiva, C. et al., Nanoparticle-mediated brain drug delivery: Overcoming blood-brain barrier to treat neurodegenerative diseases, May 18, 2016, Journal of Controlled Release, vol. 235, 34-47 (Year: 2016).*
Papa, S. et al., Selective nanovector mediated treatment of activated proinflammatory microglia/macrophages in spinal cord injury, Oct. 18, 2013, ACS Nano, vol. 7, 9881-9895 (Year: 2013).*
Smolny, M. et al., Development of non-viral vehicles for targeted gene transfer into microglia via the integrin receptor CD11b, Oct. 2014, Frontiers in Molecular Neuroscience, vol. 7, Article 79, 19 pages (Year: 2014).*
Elewa, H.F. et al., "Minocycline for Acute Neuroprotection," Pharmacotherapy, Apr. 2006, pp. 515-521, vol. 26, No. 4.
Hou, S. et al., "Novel SS-31 modified liposomes for improved protective efficacy of minocycline against drug-induced hearing loss," Biomaterials Science, Apr. 2018, pp. 1-11.
Janakiraman, K. et al., "Correction to: Development of Methotrexate and Minocycline Loaded Nanoparticles for the Effective Treatment of Rheumatoid Arthritis," AAPS PharmSciTech, Feb. 2020, 1 Page, vol. 21, No. 92.
Kay, G.W. et al., "Chronic oral administration of minocycline to sheep with ovine CLN6 neuronal ceroid lipofuscinosis maintains pharmacological concentrations in the brain but does not suppress neuroinflammation or disease progression," Journal of Neuroinflammation, Dec. 2013, pp. 1-9, vol. 10, No. 97.
Lee, C. et al., "Protective Effect of Minocycline Against Cisplatin-induced Ototoxicity," Clinical and Experimental Otorhinolaryngology, Jun. 2011, pp. 77-82, vol. 4, No. 2.
Lin, T. et al., "Blood-Brain-Barrier-Penetrating Albumin Nanoparticles for Biomimetic Drug Delivery via Albumin-Binding Protein Pathways for Antiglioma Therapy," ACS Nano, Nov. 2016, pp. A-N.
Michaelis, K. et al., "Covalent Linkage of Apolipoprotein E to Albumin Nanoparticles Strongly Enhances Drug Transport into the Brain," The Journal of Pharmacology and Experimental Therapeutics, Mar. 2006, pp. 1246-1253, vol. 317, No. 3.
Mishra, V. et al., "Targeted brain delivery of AZT via transferrin anchored pegylated albumin nanoparticles," Journal of Drug Targeting, Jan. 2006, pp. 45-53, vol. 14, No. 1, Taylor & Francis.

(Continued)

*Primary Examiner* — Craig D Ricci
*Assistant Examiner* — Paul Hoerner
(74) *Attorney, Agent, or Firm* — Lerner David LLP

(57) ABSTRACT

A composition, and method for a targeted drug delivery is disclosed in treating central nervous system injury, including blast hearing loss, traumatic brain injury (TBI) and the like, by administering a subject with nanoparticle-based minocycline formulations. The formulation contains nanoparticles encapsulating minocycline for neuroprotective effect in TBI. Albumin nanoparticle-based minocycline formulations provide enhanced delivery to brain, and reduced toxicity at minimal dosage for treating a subject suffering from central nervous system injury including blast induced traumatic brain injury (bTBI). Nanoparticle administered at minimal dose in rat blast TBI model crossed blood-brain barrier (BBB) and enhanced therapeutic concentration compared to free minocycline. Provided is an effective and safe minocycline delivery in TBI with minimal or no toxicity for neuroprotective therapy. Studies indicate performance for behavioral (acute and chronic), pathological (chronic) and hearing loss mitigation using the disclosed drug and nanoparticles in rat moderate bTBI model.

11 Claims, 20 Drawing Sheets
(15 of 20 Drawing Sheet(s) Filed in Color)

(56) References Cited

OTHER PUBLICATIONS

Nagpal, K. et al., "Evaluation of safety and efficacy of brain targeted chitosan nanoparticles of minocycline," International Journal of Biological Macromolecules, Apr. 2013, pp. 20-28, vol. 59, Elsevier.

Niknejad, H. et al., "Comparison of Different Crosslinking Methods for Preparation of Docetaxel-loaded Albumin Nanoparticles," Iranian Journal of Pharmaceutical Research, Apr. 2014, pp. 385-394, vol. 14, No. 2.

Raval, N. et al., "Development of glutathione-conjugated asiatic acid-loaded bovine serum albumin nanoparticles for brain-targeted drug delivery," Journal of Pharmacy and Pharmacology, Jun. 2015, pp. 1503-1511, vol. 67.

Robinson, A. M. et al., "Minocycline Protection of Neomycin Induced Hearing Loss in Gerbils," BioMed Research International, Mar. 2015, pp. 1-8, vol. 2015, Hindawi Publishing Corporation.

Sharma, R. et al., "Activated Microglia Targeting Dendrimer-Minocycline Conjugate as Therapeutics for Neuroinflammation," Bioconjug Chem., Nov. 2017, pp. 2874-2886, vol. 28, No. 11.

Ulbrich, K. et al., "Transferrin- and transferrin-receptor-antibody-modified nanoparticles enable drug delivery across the blood-brain barrier (BBB)" European Journal of Pharmaceutics and Biopharmaceutics, Sep. 2008, pp. 251-256, vol. 71, Elsevier.

Wrightson, W.R. et al., "Analysis of minocycline by high-performance liquid chromatography in tissue and serum," Journal of Chromatography B, Dec. 1997, pp. 358-361, vol. 706. Elsevier.

Zensi, A. et al., "Albumin nanoparticles targeted with Apo E enter the CNS by transcytosis and are delivered to neurones," Journal of Controlled Release, Mar. 2009, pp. 78-86, vol. 137, Elsevier.

Zhang, J. et al., "Minocycline attenuates noise-induced hearing loss in rats," Neuroscience Letters, Dec. 2016, pp. 31-35, vol. 639, Elsevier.

Nagpal, K. et al., "Evaluation of safety and efficacy of brain targeted chitosan nanoparticles of minocycline," International Journal of Biological Macromolecules, Apr. 2013, pp. 20-28, vol. 59, Elsevier. (2).

Zhang, J. et al., "Minocycline attenuates noise-induced hearing loss in rats," Neuroscience Letters, Dec. 2016, pp. 1-17.

Perumal, V. et al., "Transferrin-Grafted Albumin Nanoparticles for the Targeted Delivery of Apocynin and Neuroprotection in an In Vitro Model of the BBB" MDPI, Micro, Jan. 2023, pp. 84-106, vol. 3.

* cited by examiner

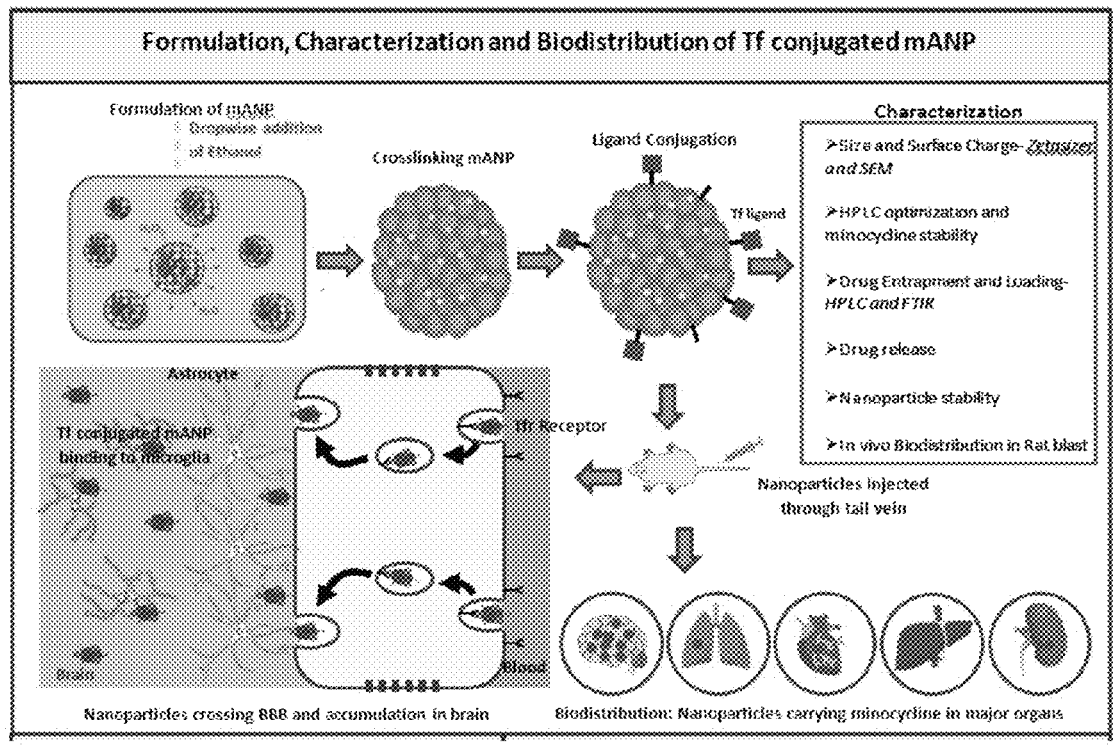
Fig.1A.
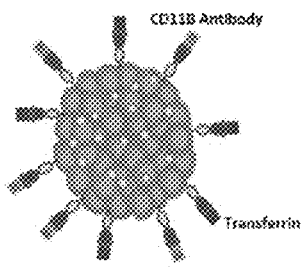
Fig.1B. Schematic of dual ligand conjugated minocycline loaded albumin nanoparticle (mDTANP).

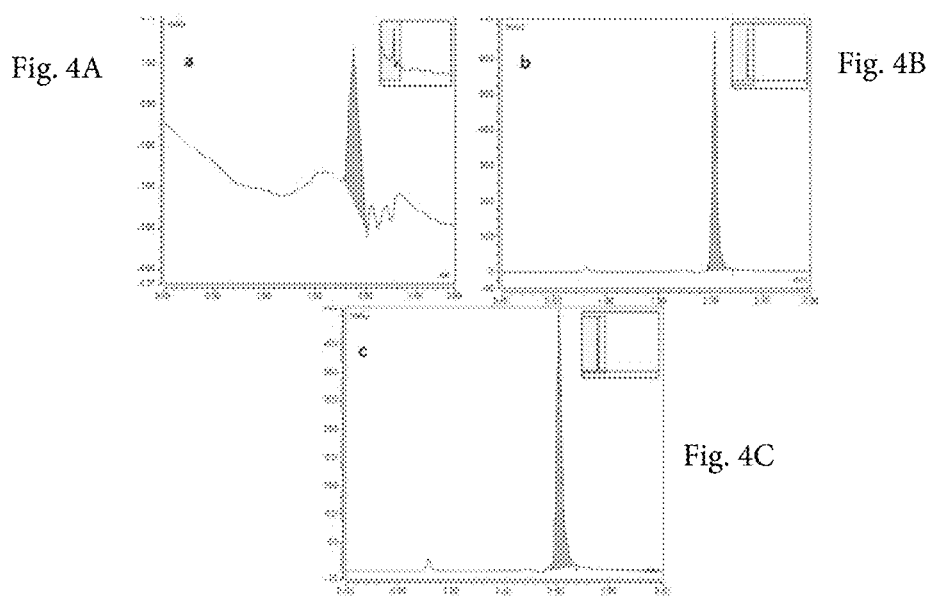
Fig. 4A-4C.
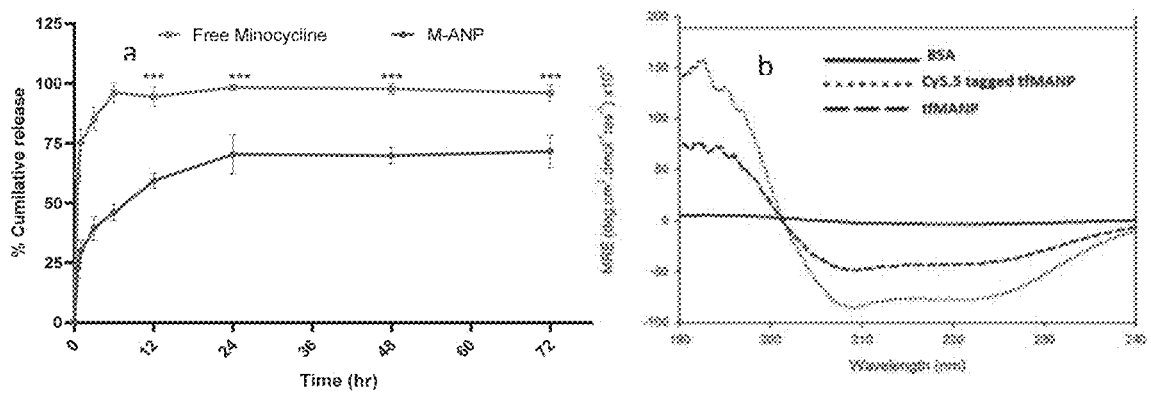
Fig. 5A
Fig. 5B

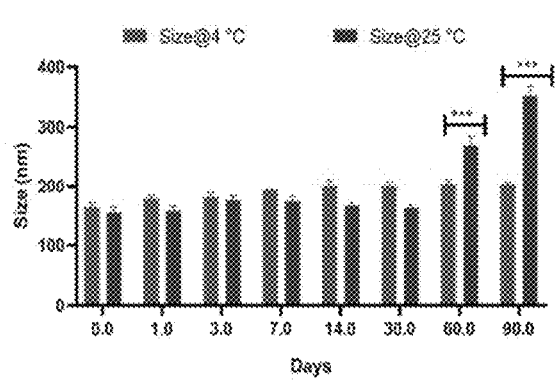
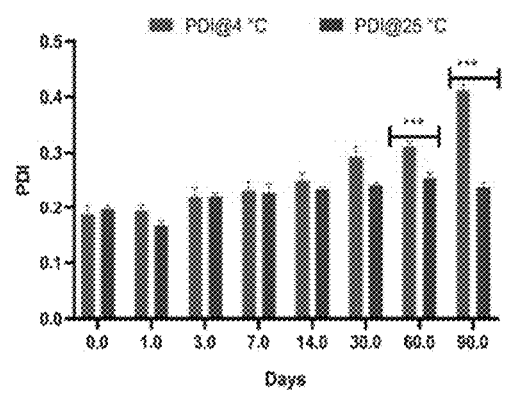
Fig. 6A          Fig. 6B
Figs. 6A-6B.
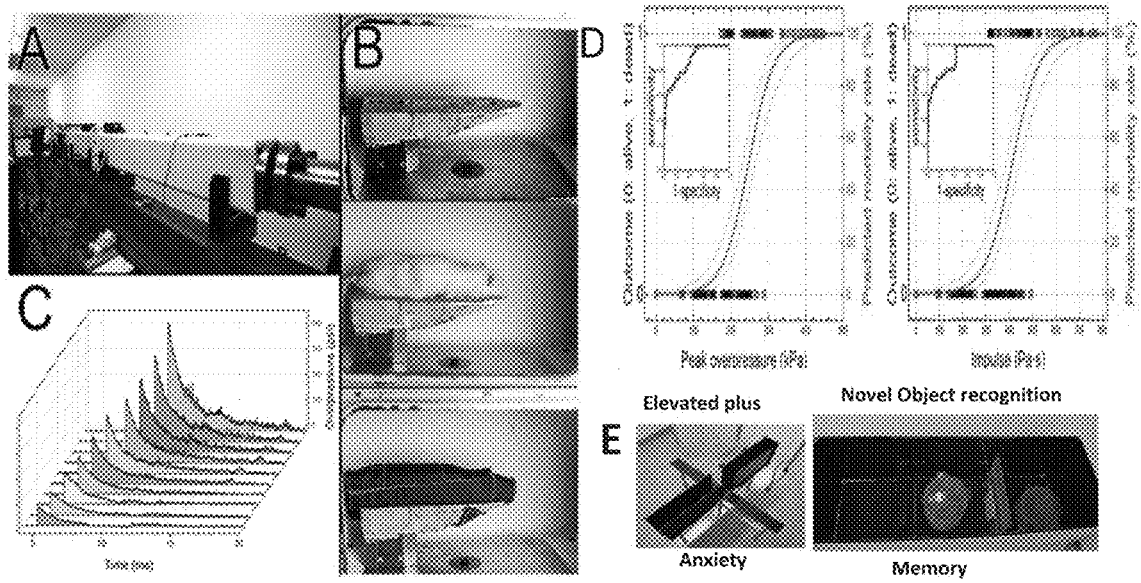
Figs. 7A-7E

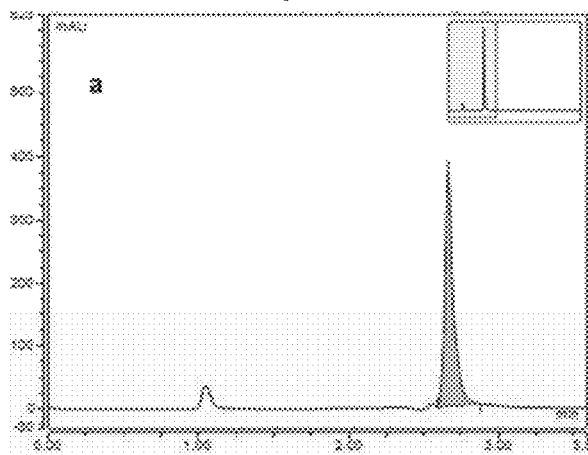
Fig. 13A
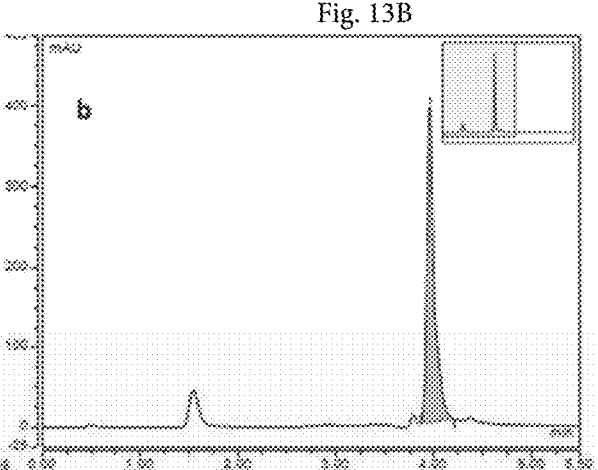
Fig. 13B
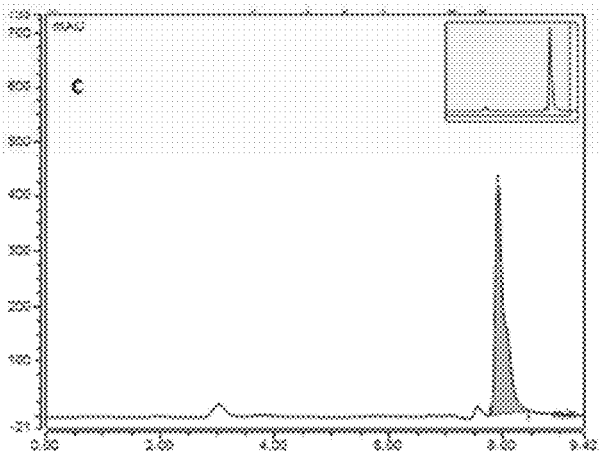
Fig. 13C
Figs. 13A-13C.

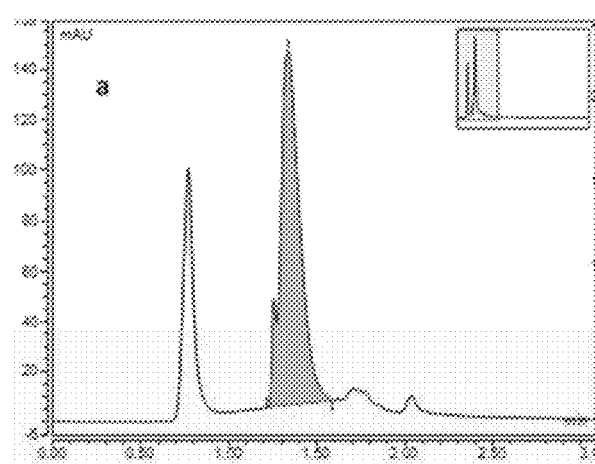
Fig. 14A
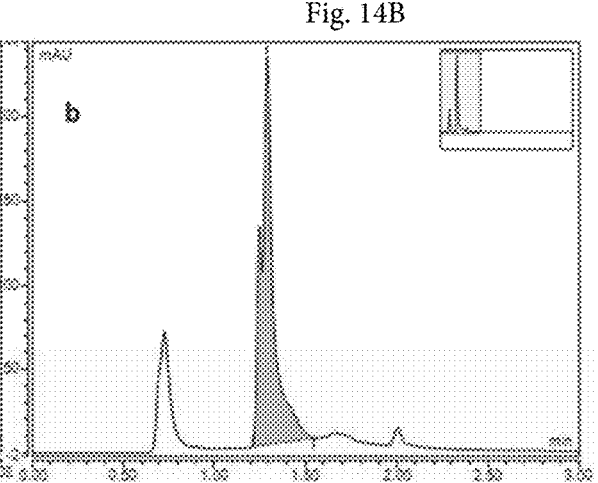
Fig. 14B
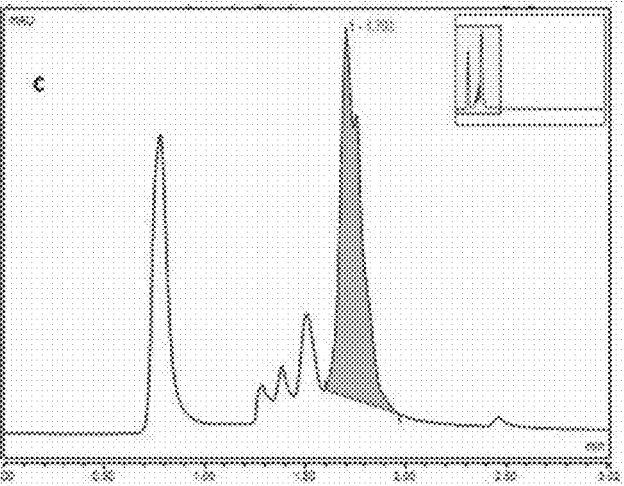
Fig. 14C
FIGS. 14A-14C.

Fig. 15A
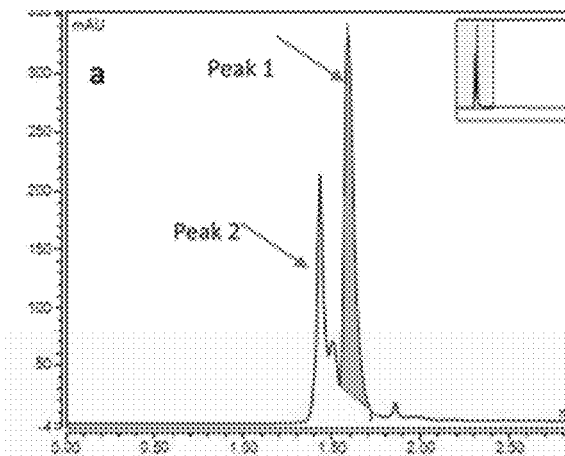
Fig. 15B
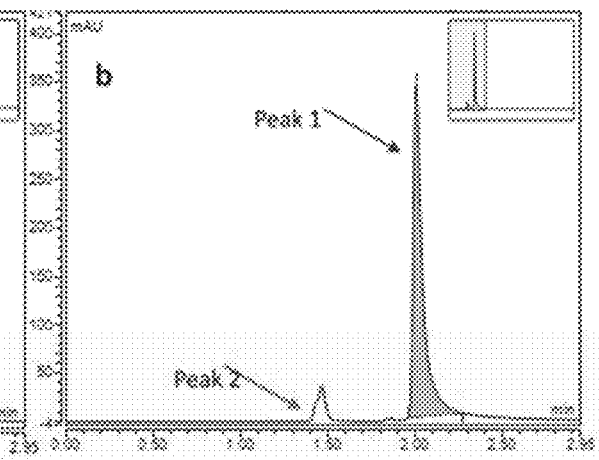
Fig. 15C
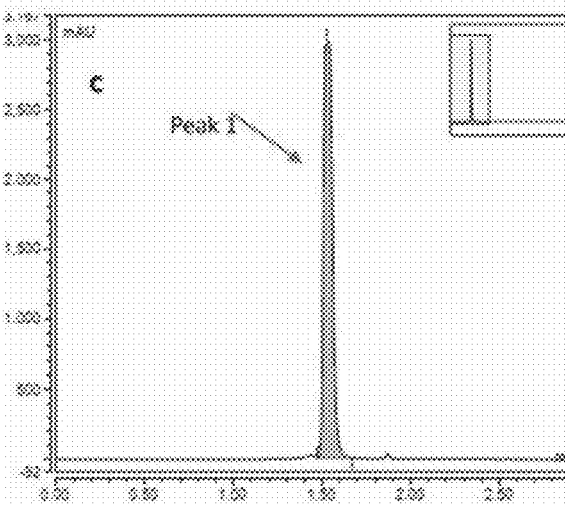
Fig. 15D
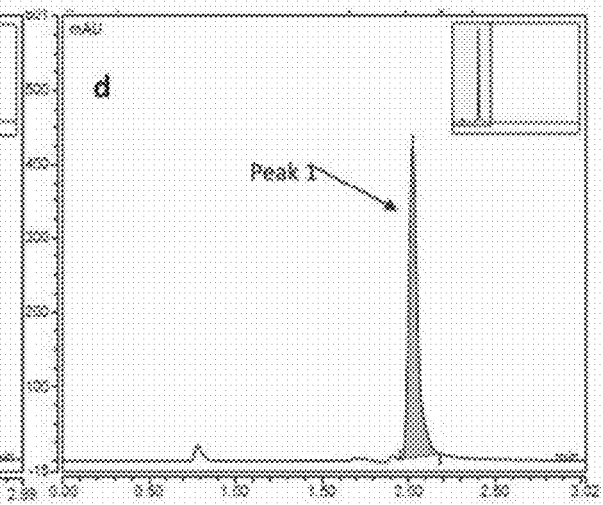
Figs. 15A-15D.

Fig. 16. Table S1 Robustness of the HPLC method to determine minocycline (n=3).

| Nominal concentration (μg/mL) | Robustness (% Recovery± % RSD) | | | | | |
|---|---|---|---|---|---|---|
| | Acetonitrile (0.2% formic acid) : Water | | | Flow rate (mL/min) | | |
| | 40:60 | 50:50 | 60:40 | 0.25 | 0.50 | 0.75 |
| 40 | 37.04±0.4 | 38.83±0.6 | 35.46±0.48 | 169.52±3.1 | 82.67±1.8 | 60.89±0.8 |
| 80 | 65.84±0.2 | 65.65±1.2 | 47.23±1.4 | 264.48±8.9 | 137.70±0.9 | 92.37±1.5 |
| 100 | 68.98±0.2 | 69.25±.89 | 46.16±1.2 | 272.91±11.7 | 140.59±0.4 | 93.07±1.8 |

TARGETED NANOPARTICLE FOR THE TREATMENT OF TRAUMATIC BRAIN INJURY AND OTHER CNS DISEASES

CROSS-REFERENCE TO RELATED APPLICATION

The present application claims the benefit of the filing date of U.S. Provisional Patent Application No. 63/180,814, filed Apr. 28, 2021, the disclosures of which are hereby incorporated herein by reference.

FIELD OF USE

The present application relates to the field of targeted albumin nanoparticle formulations of minocycline-loaded targeted nanoparticle and its enhanced brain delivery and subsequent therapeutic application for blast induced hearing loss and other injuries and diseases.

Specifically, the present application discloses a composition and treatment method using a designed targeted minocycline loaded albumin nanoparticle structure for use in brain trauma such as blast induced hearing loss, and other neurological conditions including traumatic brain injury, Parkinson's diseases, Alzheimer's disease, brain HIV, cancer, and other central nervous system (CNS) diseases.

BACKGROUND OF THE INVENTION

Blast injuries are common among the military service members and veterans. It particularly causes trauma to the auditory pathway because of the gas filled middle ear, the fluid filled inner ear and auditory brain structures are more susceptible to blast shock wave. Auditory damage is one of the primary sequelae of blast trauma, affecting immediate situational awareness and causing permanent hearing loss. Protecting against blast exposure is limited by the inability to anticipate the timing of these exposures especially in the events like terrorist attacks. As per WHO, hearing loss affects more than 466 million people.

The ear as the most susceptible, and often the first organ to sustain primary blast injury. Hearing loss (HL) and tinnitus are highly prevalent in the growing population of returning soldiers, while no effective and safe treatment is currently available. In United States, the prevalence of noise induced hearing loss (NIHL) among noise exposed workers is high: 23% with hearing loss, 15% with tinnitus and 9% with both disorders. It is estimated that more than 900 million people will lose their hearing in 2050. The economic impact of unresolved HL on society is estimated to cost $750 billion globally. Some of the most prevalent mechanisms of blast induced hearing loss are injured hair cells, cranial nerve VIII (auditory nerve) and abnormal neural plasticity. Research has been done on the peripheral auditory system (PAS) malfunction mechanism, including tympanic membrane rupture, cochlea damages and auditory nerve malfunction. Recently central auditory system (CAS) abnormalities evoked investigators' interest. Exposure to blast overpressure or high-intensity sound can cause injuries to the auditory system, which leads to hearing loss or tinnitus. The peripheral auditory system and various structures within the central auditory system are vulnerable to blast injuries, and even if the blast overpressure is at relatively mild traumatic brain injury (TBI) level. Hearing loss can arise from anywhere, given their propensity to directly damage both peripheral (PAS) and central auditory system (CAS) components including the external auditory canal (EAC), sound conduction mechanism, cochlea, cochlear nerve, and central auditory pathways. The data from blast-exposed humans suggests that blast exposure may lead to difficulties with hearing in complex auditory environments, even when all the peripheral hearing sensitivity is near normal. Race and co-workers conducted experiments on rodents exposed to blast and blast-induced noise, and concluded that the auditory system (both the PAS and the CAS) is more vulnerable to blast (shock and noise) compared to only noise, which predominantly showed only the PAS effects. Further was revealed by researchers that the existence of hyperactivity in the dorsal cochlear nucleus (DCN), inferior colliculus (IC), and auditory cortex (AC) along with increased neuronal synchronization and tonotopic remodeling in the AC is identified. These findings shed light on that both PAS and CAS are both vulnerable to blast trauma.

Treatment for such blast hearing loss injuries have been met with several difficulties. For example, one drug previously investigated, minocycline, is limited by its partial efficacy, optimal dosages form and routes of administration, and lack of targeted delivery to peripheral and central auditory systems for hearing preservation. A therapeutic approach and delivery method is in great need.

There is no approved treatment for blast induced hearing loss to date. Many potential treatments for hearing loss have been met with limited success. Stem cell therapy and neurotrophic factors were used in animal models to repair or regenerate the damaged structure and had limited success. Several therapeutic agents may partially protect hearing were examined in animal models of chemical ototoxicity and noise mediated deafness. Drugs such as steroids, etanercept, D and L-methionine, pifithrin-alpha, adenosine agonists, melatonin and kenpaullone (a cyclin dependent kinase 2 (CDK2) inhibitor) have been reported to show efficacy against cisplatin ototoxicity in animal models. Free radical scavenger allopurinol has been found to provide short term protection from hearing loss in guinea pigs.

Lidocaine, a local anesthetic, and anti-arrhythmic agent, is also known both as a tinnitus and as a pain-suppressing drug, however, has drawbacks. The sites of action in tinnitus suppression are in the cochlea as well as in the central auditory nervous system. Specifically, administration of 2,4-disulfonyl alpha-phenyl tertiary butyl nitrone (HPN-07) and N-acetylcysteine (NAC) has been shown to block some of the auditory pathological outcome of exposure to blast overpressure or other impact injury in animal model. In addition, a combinatorial regimen HPN-07 and NAC can significantly reduce pathologic Tau accumulation and alleviate the neurodegeneration in the cochlea. Reduction in blast-induced neurodegeneration risk of tinnitus by approximately 50% was shown wherein cochlear ribbon synapse preservation or repair and normalization of the expression patterns of homeostatic gating factors in the central auditory pathway were apparently involved. However, these therapeutic approaches lack a consistent therapeutic delivery method that can achieve longer systemic circulation, pass through some biological barriers, and specifically targets desired sites.

Another potential drug for treating hearing loss is Minocycline, an FDA approved semi-synthetic tetracycline derivative, that has both anti-inflammatory and neuroprotective properties. It is worldwide approved inexpensive tetracycline derivative that has antimicrobial, anti-inflammatory, anti-oxidant, antiapoptotic properties and identified with various neuroprotective properties. Previous reports indicated that minocycline exerts neuroprotective effects against a wide variety of neurodegenerative diseases, such as amyotrophic lateral sclerosis and Huntington's disease. More importantly, several other work revealed that minocycline attenuated noise-induced and ototoxic drug (cisplatin, neomycin, and gentamycin) hair cell loss (in a Guinea pig model) and in vitro models. Some studies have investigated a combination use of minocycline with aminoglycoside antibiotics for bacterial infection could also be evaluated as a means of ameliorating ototoxic hearing loss. However, these therapeutics are not effectively delivered to the brain and inner ear. There are many obstacles to drug delivery to the inner ear, of which the main obstacles are the blood brain barrier (BBB). Again, these therapeutic approaches lack a consistent therapeutic delivery method that can achieve longer systemic circulation, pass through some biological barriers, and specifically targets desired sites.

In addition, traumatic brain injury (TBI) contributes to a major cause of death, disability, and mental health disorders. Most TBI patients suffer long-term post-traumatic stress disorder, cognitive dysfunction, and disability. The underlying molecular and cellular mechanisms of such neuropathology progression in TBI remain elusive.

TBI accounts for approximately one-third of all injury-related deaths in the United States. Over the past decade, there has been a sharp increase in TBI incidents resulting from combat-related injuries as well as insurgent activities on civilian population. The direct medical costs of TBI are in the billions of dollars. Although there has been a lot of effort focusing on treatment modalities for TBI, there has not been much success in developing a therapeutic strategy to treat TBI-associated deficits.

Currently, there are limited treatments to neurodegenerative disorders associated with TBI and no clinically approved drug to treat TBI. Neurodegenerative disorders associated with TBI impose enormous health and societal burden worldwide. One reason why there is currently no clinically approved drug to treat TBI is due to the inability to deliver therapeutics to the brain. Based on pre-clinical and clinical studies, high plasma protein binding and increased doses of minocycline, a class of medications called tetracycline antibiotics. (~20-100 mg/kg multiple doses vs ~3 mg/kg per day clinically to treat infectious and chronic inflammatory diseases) is required to achieve neuroprotective effects in most CNS models. Current dosage protocols of minocycline have resulted in serious side effects and neurotoxicity.

Current methods and compositions have fallen short in achieving required bioavailability (therapeutic concentration level) at a dose that safely can be administered. Bioavailability in the brain permits the desired pharmacological concentration and eliminates delirious side effects. Widely-acknowledged barriers such as the blood-brain barrier (BBB) and the extracellular space of brain parenchyma are known for preventing nanoparticles (NPs) from reaching the targeting site. If the NPs unselectively distribute in the whole brain, the improvement of treatment outcome caused by elevated drug concentration might accompany even worse side effect to CNS. Hence, a targeting approach using nanoparticles is highly essential for initial transport of nano-cargo across the BBB and subsequently to target specific cell in injured brain region.

A number of dual ligand targeted delivery approach has been explored in the past for treatment of various brain disorders. However, these approaches has found limited success. Noted examples are (1) in a HIV model, the dual antibody-modified chitosan/small interfering RNA (siRNA) nanoparticles to deliver siRNA across the blood-brain barrier (BBB) and then targeting HIV-infected brain astrocytes was studied; (2) analgesic effect on CNS was studied using human serum albumin nanoparticles (HSA NPs) coupled to transferrin or TfR-mAb displayed a significant loperamide transport across the BBB into the brain and CNS analgesic effect; (3) combination of a folate receptor (tumor cells) and a TfR (BBB endothelial cell), or a TAT receptor (tumor cells) and a transferrin receptor (TfR, BBB endothelial cells). Both demonstrated the increased brain tumor uptake of therapeutics in vitro and extended survival compared to single targeting therapy, however, still had drawbacks such as targeted delivery; and (4) angiopep-2 and EGFP-EGF1 dual modified nanoparticle for specifically targeting neuroglial cells in normal brain because the low-density lipoprotein receptor-related protein (LRP) (receptor of angiopep) is overexpressed on the BBB. Still this delivery method was also limited.

Therefore, there still exists a critical need for a novel therapeutic strategy and composition that allows for effective therapeutic treatment of TBI, blast hearing loss, and other CNS diseases without the adverse side effects of current methodologies. In addition, there is a need for a methodology that may be expanded to other similar brain related conditions using similar modalities without the negative consequences of current therapies.

SUMMARY OF THE INVENTION

Compared to the above prior attempts, the presently disclosed composition and method solves the problems of current state of the art, meets the above requirements, and provides many more benefits. Disclosed is a minocycline loaded targeted nanoparticle that can be formulated and optimized using albumin. Established are targeted nanoparticles that highly accumulate in the brain as compared to free minocycline in the bTBI model.

In one aspect, examined was the therapeutic effect of minocycline and its nanoparticle formulation in moderate blast induced hearing loss rat model through central auditory system (CAS). The nanoparticle formulations were prepared by modified desolvation method and then intravenous administered at reduced dose and frequency than regularly administered toxic dose. Hearing thresholds were recorded by auditory brain response (ABR) and pathological changes of central auditory system were analyzed at acute and chronic periods by immunohistochemistry. Effectively delivering cochlear hair cell protection drugs to the brain and inner ear is the key to hearing loss prevention and protection. The present disclosure achieves this objective that no other current therapeutic system has provided.

After moderate blast exposure, rats had hearing impairment as determined by ABR at 7- and 30-days post exposure. Rats treated with free minocycline had the significant effect of reducing the ABR threshold compared with blood brain barrier (BBB) targeted transferrin tagged nanoparticle and PEGylated (non-targeted) nanoparticle acutely. In chronic condition, free minocycline also showed the significant reduction in ABR threshold, Comparatively, both the BBB targeted transferrin tagged nanoparticle and regular (PEGylated non-targeted) nanoparticle formulation improved hearing loss.

In central auditory system, it was found that minocycline nanoparticles ameliorate excitation in inferior colliculus (IC); and astrocytes and microglia activation after the blast exposure is reduced by minocycline nanoparticles administration. It easily cross BBB barrier due to lipophilic in nature and also have the ability to restore BBB breakage. Because of this property, minocycline can have systemic effect both in the peripheral and also central systems, making this an efficient drug for blast induced hearing problems and the like. The results described herein indicate that in moderate blast induced hearing loss, minocycline and the described nanoparticle formulation exhibited the optimal therapeutic effect on the recovery of the ABR impairment and a protective effect through central auditory system. This disclosure provides never before seen evidence that both free minocycline and the described nanoparticle formulation have therapeutic effect on blast induced hearing loss.

In another aspect, the nanoparticle formulation was administered at a minimal dose in rat blast TBI model, crossed the BBB and enhanced therapeutic concentration compared to free minocycline. Behavioral (acute and chronic), pathological (chronic) and TBI induced hearing loss mitigation studies are being performed using the drug and nanoparticles in rat moderate bTBI model.

Among other benefits, the disclosed method and composition mitigates hearing loss using free minocycline and the disclosed nanoparticle formulation. The targeted albumin nanoparticle formulation of minocycline is a loaded targeted nanoparticle. It has enhanced brain delivery and subsequent therapeutic application in moderate blast TBI model as shown in the present novel study (as indicated in FIG. 1 schematic). Nanoparticle administered at a minimal dose in rat blast TBI model exhibited the BBB crossing and enhanced therapeutic concentration compared to free minocycline. To the best of the present investigator's knowledge, there has been no report on formulation, characterization and therapeutic effect of minocycline loaded albumin nanoparticles in moderate bTBI model. Therapeutic effect of free minocycline was also not explored in the moderate bTBI model.

Further, it was determined that the same nanoparticle structure can also be applied in other neurological conditions including traumatic brain injury, blast hearing loss, Parkinson's diseases, Alzheimer's disease, brain HIV, cancer and more. The designed targeted minocycline loaded albumin nanoparticle is applied in moderate bTBI model with improvement of enhanced bioavailability and therapeutic effect. Major modification of the nanoparticle from existing technologies is that loading of minocycline in albumin nanoparticles (no literature report is existing).

Another aspect of the present invention is evaluation of minocycline free molecule, minocycline loaded albumin nanoparticle (MANP) and targeted MANP (tfMANP) for neuroprotective effects in terms of behavioral, pathological, and biochemical analysis (no literature report is existing) in moderate blast TBI in rat model. Further toxicity of the minocycline was also evaluated in vivo comparing both free minocycline and nanoparticle version.

In one aspect, the proposed modification of the targeted nanoparticle, minocycline loaded albumin nanoparticle (MANP), is exploited both receptor-mediated endocytosis in vasculature and glial cells; and transiently leaky BBB to enhance the bioavailability at injury site and reduce the toxicity of the drug. Loperamide loaded albumin nanoparticles with covalently bound transferrin or the OX26 or R17217 antibodies was capable of transporting loperamide across the BBB and induced significant anti-nociceptive effects.

Antibodies to the integrin receptor CD11b, also known as complement receptor 3 (CR3), have the potential to be used for targeting immunogens to microglia. The Tf conjugated BSA nanoparticle was formulated in three steps.

In the first step, minocycline loaded albumin nanoparticle (MANP) was prepared using a modified desolvation method. Depending on the implementation, 10% BSA (w/v) in HPLC grade water was stirred (at 600 rpm) with 7.5% of minocycline (w/v) at room temperature for drug absorption onto albumin. After 1 h of continuous stirring, the pH value was adjusted from 7.5 to 8.5 using 0.1 M NaOH. The mixture was then desolvated through addition of a suitable amount of ethanol, using a peristaltic pump at a rate of 1 ml/min under stirring (at 600 rpm). Ethanol addition was sustained till turbidity point and residual ethanol was removed by a rotary evaporator at 4° C. Then, the formulated minocycline-loaded nanoparticle was stabilized by crosslinking with 8% glutaraldehyde solution for 24 hr. The nanoparticle in solution was ultra-centrifuged (Sorvall LYNX 6000, Superspeed Centrifuges) at 36288 g force for 40 min.

Secondly, 2-iminothiolane solution was added to bind a sulfhydryl group to the transferrin. Transferrin was dissolved in phosphate buffer (1 mg/ml at pH 8.0) and incubated with 12.8 µl (50.85-fold molar excess) of 2-iminothiolane solution (6.9 mg in 1.0 ml phosphate buffer, pH 8.0) in the dark for 2 h at 20° C. under constant shaking (500 rpm). Thereafter, the thiolated transferrin was purified by PD-10 Columns Sephadex™ G-25 M, using phosphate buffer (pH 8.0) as eluent.

Thirdly, NHS-PEG-MAL-5000 solution in 10-fold molar excess was introduced to the nanoparticles to cross-link activate them. To conjugate the NPs, 500 µl of thiolated and purified transferrin solution was added to 500 µl of reactive BSA NPs. The mixture was incubated under shaking for 24 h at room temperature. Thiolated transferrin excess was removed by 2-fold nanoparticle centrifugation, redispersed in water and lyophilized. Precipitate obtained from the centrifugation was washed with pure water three times and then freeze-dried to obtain brownish fine powder of Tf conjugated MANP. For further characterization, a stock suspension of NP was used. Similarly, the drug-free ligand conjugated empty albumin nanoparticle (tfEANP) was also prepared.

Conjugation of Cy5.5 to BSA Nanoparticles

The near-infrared (NIR) fluorophore Cy5 was labeled on FAHSA-RESNPs to investigate the in vivo distribution of NPs in tumor-bearing mice. BSA nanoparticles was conjugated to Cy5.5 according to routine protocol. A reaction between BSA and the Cy5.5-NHS ester (Invitrogen, Carlsbad, Calif., USA) at a molar ratio of 1:2 was performed in the dark at room temperature for 1 h. Unconjugated dye was removed by dialysis against phosphate-buffered saline (PBS) using a Slide-A-Lyzer membrane cassette (3,500 MWCO) for up to 18 h at 4° C. Dialyzed samples were filtered through a 0.2-µm syringe filter, to ensure quality before use.

Two separate approaches were utilized to redisperse the lyophilized MANP, physical shaking and sonication. Manually shaking method was applied using weighed quantity of lyophilized NP with phosphate buffer saline pH 7.4. The nanosuspension was subject to gentle shaking for 2 min to redisperse the solution and then immediately measured for particle size using a Malvern zeta sizer. After gentle shaking for 2 min the nanosuspension was subjected to particle size measurement using Malvern zeta sizer. Micrometer sized particles were considered too non-dispersible. Sonication method was applied with lyophilized NP in phosphate buffer saline pH 7.4 for 2 min using a bath sonicator and redispersibility.

Characterization of the Nanoparticles

Mean particle size, particle-size distribution and zeta potential of the nanoparticles were measured using Zeta sizer (malvern). Particle size and zeta potential measurements were conducted on freshly prepared dispersions of nanoparticle stock suspension (1 mg/mL) in PBS at pH 7.4. The results were reported as average values from triplicate runs of three independent experiments for each sample. The structural morphology of nanoparticles was determined by field emission SEM (LEO 1530VP). For SEM imaging, Nanoparticles in ethanol (20 μL) were placed and converted into powder on the surface of carbon substrates. Prior to analysis, samples were placed onto metal stubs using double-sided adhesive tape, sputter coated with gold/palladium to make them electrically conductive and suitable for SEM imaging (EM JSM-7900F, JEOL). For TEM analysis, 10-20 μL of the NP solutions in ethanol was placed on a 200-mesh copper grid coated with carbon. The copper grid was allowed to dry for 2 hours at room temperature before imaging (JEM-F200/F2). FT-IR transmittance spectra of the nanoparticles were obtained using Spectrum 100 FTIR spectrometer (PerkinElmer). Data were collected in the wave number range of 400-4000 cm$^{-1}$ at a resolution of 1/cm was measured.

Optimization and Validation of HPLC Settings and Acquisition Conditions

Prior to the encapsulation efficiency and drug release study, the HPLC method was optimized and validated on a Thermo Fisher UltiMate 3000 HPLC, equipped with a photodiode array detector. International Conference on Harmonization (ICH) based recommendations were applied to validate the HPLC method. RP C18 analytical reverse phase column (125 mm×4 mm, 5 μm), maintained at ±25° C., was used with isocratic mode. A mixture of acetonitrile- and water mixture, acidified with 0.02% formic acid (25:75 v/v) was used as the mobile phase at a 1 mL/min flow rate. All the samples were filtered through a 0.2 μm filter, of which 10 μL was automatically injected into and detected at 273 nm wavelength for a duration of 10 minutes. The obtained chromatographic data was further analyzed using Chromeleon CDS software. Minocycline, in concentrations ranging from 0-200.0 μg/mL were used to construct a calibration curve. Minocycline was added to supernatant (blank nanoparticle formulation) for the standard samples. The number of theoretical plates and the tailing factor were estimated for the system suitability by using six replicates of standard minocycline solution at the concentration of 80 μg/mL.

Further, linearity, specificity, precision, accuracy, robustness, limit of detection and quantification were measured as major validation parameters for ideal HPLC measurement. To estimate the specificity of the HPLC method, a comparison was conducted between the chromatograms of the blank nanoparticles' supernatant and that of the minocycline standards. Precision (Intra- and inter-day variations) was determined using standard samples at concentration (40, 80, and 100 μg/mL) and expressed in terms of the relative standard deviation (% RSD). To determine the accuracy of the measurement, standard samples of concentration (40, 80, and 100 μg/mL) were compared to the calculated percent recovery of minocycline. By changing the flow rate (0.25, 0.5, and 0.75 mL/min) and ratio (acetonitrile and water; 40:60, 50:50, and 60:40 v/v) of mobile phase, robustness of the HPLC method analyzed using the standard samples (40 μg/mL, 80 μg/mL, and 100 μg/mL) concentration in triplicate. Any changes in these parameters were assessed by RSD and percent recovery. Further, limit of detection and quantification were also calculated from slope of calibration curve and least standard deviation obtained from chromatogram.

Minocycline Stability

Measuring the drug molecule's stability is essential as it directly impacts the formulation strategy when designing the drug-loaded nanoparticle. Minocycline was subjected to acid and base mediated degradation to understand the stability of minocycline and specificity of the developed HPLC method. 1 M HCL and 1 M NaOH were added to separate minocycline hydrochloride solution and stored for 1 h at RT before HPLC analysis. Similarly, a solution of minocycline and H$_2$O$_2$ (30% v/v) was allowed to incubate for 1 h prior to HPLC analysis. Light mediated minocycline degradation consisted of visible light exposure on the drug over a period of 24 h.

Entrapment Efficiency and Loading of Minocycline in Tf Conjugated MANP

The amount of minocycline entrapped in the albumin nanoparticle was quantified by using a validated HPLC method. The quantity of drug encapsulated was measured through indirect means, by quantifying amount of minocycline in supernatant obtained after ultra-centrifugation. Further, the supernatant was dialyzed (20 kDa) to remove the traces of proteins. Briefly, 5 ml of supernatant was transferred into dialysis cassette (10 ml, cutoff 20 KDa) and then the cassette was placed in 200 mL of beaker with HPLC grade water. Before putting the sample into dialysis cassette, the membrane of the cassette was hydrated with water. The media was stirred at 250 rpm overnight and 1 ml of dialysis media was withdrawn for HPLC analysis vial.

Encapsulation efficiency=(total minocycline−minocycline in the supernatant)/total minocycline×100% For minocycline loading efficiency, known quantitative albumin nanoparticle was dispersed in purified water added as needed. The nanoparticle suspension was sonicated for 30 min and filtered through a 0.25-μm membrane (Whatman® membrane filters nylon pore size 0.2 μm, diam. 25 mm) and quantified by HPLC method. Drug Loading R=(Weight of minocycline in nanoparticles/Total weight of nanoparticle)×100%.

In Vitro Minocycline Release from Nanoparticle

The in vitro release profile of minocycline from the Tf conjugated MANP was investigated by dialysis method using phosphate-buffered saline (PBS; 0.01 M, pH 7.4) as the release medium. Briefly, 1 mL of minocycline solution or Tf conjugated MANP suspension (1 mg/ml) in PBS was added in a dialysis bag (MWCO 8,0000 Da) and incubated in 200 mL of release medium at 37° C. at the shaking speed of 100 rpm. For certain time points, a 0.5 mL aliquot was withdrawn (0 to 72 hrs) and replaced with an equal volume of fresh release medium. The samples were then subject to HPLC analysis, as described above, and shielded from light exposure during the process. These samples were analyzed in triplicate.

Stability of Tf Conjugated MANP

Stability study was performed using lyophilized Tf conjugated MANP stored at 4° C. and 25° C., at predefined days (0, 1, 3, 5, 7, 14, 21, 28 (1 month), 60 (2 months), and 90 (3 months)). Lyophilized minocycline-loaded albumin nanoparticles were suspended with 1 ml of PBS, and all samples were analyzed for changes in the particle size/PDI and surface charge.

Circular Dichroism Spectra of BSA, tfMANP and Cy5.5 Tagged MANP

To determine the characteristic preservation of the alpha helical secondary structure, Circular Dichroism was performed using a Jasco J810 spectropolarimeter (MD, USA). Circular dichroism (CD) spectra of BSA, tfMANP and cy5.5 tagged MANP and were recorded at a concentration of 500 µg/mL in PBS buffer using a Dichroism Spectropolarimeter (J-810, Jasco International Co., Ltd., USA). The far UV region was scanned between 190 nm and 250 nm. All the data were buffer corrected and converted to molar residual ellipticity (MRE). MRE was calculated by $$[\theta] = \frac{\theta x m}{c x n_r x l}$$

where θ is MRE in millidegrees, m is molecular weight in g/mol, c is concentration in mg/mL, l is the pathlength of the cuvette in cm, and $n_r$ is the number of amino acids in the peptide.

In Vivo Biodistribution of Targeted Tf-MANP in Blast TBI Rat Model

Animals: Ten-week-old male Sprague-Dawley (Charles River Laboratories) rats with 350±50 g were used in accordance with protocols approved by Rutgers University Institutional Animal Care and Use Committee (IACUC approval: PROT0201900142). The animals were housed with free access to food and water in a 12-h dark-light cycle at 22° C. Rats were divided into four groups (n=5; sham controls, blast and two treatment animals exposed to a moderate blast of 180 kPa). The time points for minocycline (3 hrs) and targeted nanoparticle (24 hrs) were chosen because half-life of minocycline is 2-3 hrs in rat models and extended systemic circulation of targeted nanoparticle.

Blast injury: Rats were subjected to a single blast wave at the Center of Injury Biomechanics, Materials and Medicine (New Jersey Institute of Technology, Newark) in the 9-inch square cross section shock tube. In this study used were-4-5 rats in each experimental group (power value of 0.8, α=0.05) based on a power analysis. Before the blast exposure, all animals (controls, blast, blast+Treatment) were anesthetized with 5% isoflurane, then released into a chamber containing 95% air and 5% $CO_2$. Rats were placed horizontally inside the shock tube (in a 6 m long shock tube with 9-inch square cross-section) located 2.8 m from the point where the shockwave was generated at one end of the tube and 3.05 m from its exit. Rats were strapped securely to the aluminum plate using a cotton cloth wrapped around the body. The cloth provided no protection against the shockwave but prevented excessive motion of head.

The pressure waveform was recorded using PCB Piezotronics sensors model 134A24 (Depew, NY) at the 1.0 MHz sampling frequency for about 5 ms. Rats were subjected to a single shock wave with moderate blast 180 kPa. Sham control rats received anesthesia and noise exposure without blast exposure—i.e., anesthetized animals were placed next to the shock tube, and then a single blast was applied. Following blast injury, animals were closely observed for any signs of apnea, loss of motor coordination and modified neurological severity score (NSS) was evaluated five minutes post-exposure. None of the animals included in this study displayed NSS scores that differed from sham animals.

Treatment regime: Targeted nanoparticles and free minocycline were intravenous injected at the dose of 3 mg/kg after 4 hrs of exposing rats to a single moderate blast (180 kPa). Samples were collected after 3 hrs and 24 hrs for minocycline and nanoparticle treated groups, respectively.

Minocycline Extraction and Biodistribution Analysis by HPLC

Prior to transcardial perfusion, rats were anesthetized with a mixture of ketamine and xylazine (1:10 ratio), perfused either 15 min or four hours post-blast. Blood (about 3 ml) was collected by cardiac puncture (left ventricle) and allowed to settle in vacutainer tubes (BD Bioscience) containing 3.2% sodium citrate for 10 minutes. Plasma was separated from blood by centrifuging at 2000 g. After the blood samples collection, the rats were transcardially perfused with PBS for isolation brain, liver, lungs, kidneys, heart, and spleen. The tissues were homogenized, and the minocycline was extracted with sodium phosphate sulfite buffer and ethyl acetate using liquid phase extraction. Plasma aliquots (500 µl), tissue (homogenized) and standards (0.08 to 10.12 µM minocycline in plasma) were diluted with 1000 µl of sodium phosphate sulfite buffer (2.4 M disodium hydrogen phosphate, 4.0 M sodium sulfite, pH 6.5) and thoroughly mixed with 5 ml of ethyl acetate. After centrifugation to separate the phases, the aqueous phase was frozen, and the organic phase was poured off into 50 µl of 0.2% ascorbic acid and 0.1% cysteine in methanol. Samples were dried at 39° C. under nitrogen, and the residue was dissolved in 300 µl of HPLC mobile phase. After centrifugation, 12,000 rpm, 10 min, 50-µl aliquots were injected onto HPLC column and eluted with running buffer at 1 ml/min. Minocycline, retention time 2.1 to 2.4 min, was detected at 270 nm. The minocycline concentration (per gram of tissue) in the supernatant was analyzed by using optimized HPLC method.

Accumulation of Nanoparticle Brain Parenchyma In Vivo bTBI Model

Animals: Ten-week-old male Sprague-Dawley (Charles River Laboratories) rats with 350±50 g were used in accordance with protocols approved by Rutgers University Institutional Animal Care and Use Committee (IACUC approval: PROT0201900142). The animals were housed with free access to food and water in a 12-h dark-light cycle at 22° C. Rats were divided into three groups (n=4; blast and two treatment animals exposed to a moderate blast of 180 kPa). Nanoparticles were injected after 30 min of blast injury and 6 hrs time points for Non targeted and targeted nanoparticle were chosen.

Immunofluorescence Staining

Blast TBI rats were injected with fluorescently labelled Targeted nanoparticles and Non targeted nanoparticle by tail vein. After 4 h, the brain were harvested Brains were fixed with 4% paraformaldehyde for 24 h, incubated in a 30% sucrose solution for 72 h, and then stored at 80° C. until sectioning. After blocking with 10% donkey serum for 1 h at room temperature, sections were incubated with microglia/macrophages (rabbit anti-Ibal, Wako Laboratory Chemicals #019-19741, 1:2,000, overnight at 4° C.), astrocytes (rabbit anti-GFAP, Dako Z0334, 1:5,000, overnight at 4° C.), or neurons (mouse anti-beta III tubulin-Alexa Fluor® 488, Abcam #169556, 1:600, 4 hrs at RT). Rabbit primary antibodies were detected using goat-anti-rabbit-Alexa Fluor® 488 (Life Technologies, 1:500, 1 hr at RT). Coverslips were mounted using Dako fluorescence anti-fade mounting media. Sections were washed and incubated with secondary antibodies for 1 h. Sections were washed, and images were captured using a Zeiss Axiovert 200M microscope.

Behavioral Study

Minocycline, tMANP and MANP treated moderate bTBI rat model.

Rats were divided into five different groups; sham control, blast Minocycline, tMANP and MANP. Rats were exposed to moderate blast group (180 kPa) and administered with Minocycline, tfMANP and MANP (3 mg/kg of minocycline for 4 days).

Novel Object Recognition Test

This test was used to measure short-term memory loss, specifically object recognition in single & repeated blast groups. Rats were assessed for cognitive decline at acute and chronic time points (7th and 35th day) after blast exposure. Briefly, NOR consists of three phases; habituation, familiarization, and testing phase. In the habituation phase, each rat was allowed to acclimatize in the testing chamber for 5 mins 1 d prior to the testing phase. On testing day, each rat was placed in the testing chamber which has two identical object, known as familiarization stage. In this phase animal allowed to explore the new identical objects for 10 min. After familiarization phase, rats were kept back in housing cage for an hour. After an hour interval, each rat again exposure two objects in which one object replaced with novel one (Testing phase). Rats allowed to explore two objects; familiar& novel object for 5 min. The total time spent exploring each of the two objects was recorded by using ANY maze software. A discrimination and preference index for the novel object is used to measure recognition memory or short-term memory loss.

Open Field Test

The open field test was used to assess anxiety and exploratory behavior in single & repeated blast groups at acute and chronic time points (7th and 35th day). Rat was placed in the center of an empty open field box with the dimensions of (60×60×60 cm). The rats were allowed to explore the open arena for 5 min and the animal movements tracked by ANYMaze software. During the task, the open field was divided into center and corner zone, which were drawn in ANYmaze software. In this task anxiety was determined by counting time spent in center zones.

Elevated Plus Maze

This test was used to determine anxiety at acute and chronic time points (7th and 35th day) after blast exposure. The elevated plus maze is a plus-shaped apparatus with four arms: two open and two closed arms. Each arm is 110 cm in length and the entire apparatus elevated 60 cm above the ground. Rats were placed at the center of the maze facing towards open arm and given 600 s to explore the maze. Anxiety/depression like behavior was determined by counting the number of entries into each arm, and calculating the total time spent in each arm in the maze (and in each arm). Animal movements in the maze was recorded by using the video camera positioned over the maze and the data analyzed in ANYMaze software.

Minocycline, Non-Targeted MANP and Targeted tfMANP Treatment in Blast-Induced Hearing Loss: Auditory Brainstem Response (ABR)

Cochlea conditions and inferior colliculus integrity were examined by ABR at acute and chronic time points in sham, blast, minocycline, non-targeted MANP and targeted tfMANP group. ABR thresholds were recorded as the parameter of functional evaluation of neuronal circuit between cochlea and inferior colliculus. For acute and chronic time point, animals were examined for the tympanic membrane (TM) rupture conditions, TM ruptured animals were excluded from the ABR examination.

Then animals were initially anesthetized. Three platinum-coated tungsten electrodes were inserted in the vertex, below the ipsilateral pinna, and in the hind leg muscles for the positive, negative, and ground positions, respectively.

Click and tone-burst stimuli at 4, 6, 8, 10, 12, 14, 16, 18, 20 kHz were delivered through TDT M1 for free field operation. Stimuli were played from 100 to 5 dB with 5 dB stepwise decrease.

ABR signals were amplified, band-filtered from 0.3 to 3 kHz, notch-filtered at 60 Hz, and averaged 300 times for click and tone-burst stimuli, respectively. ABR threshold was defined as the lowest sound stimulus level at which ABR waves can be identified.

In Vivo Toxicity of Minocycline, Non-Targeted MANP and Targeted tfMANP

As a drug delivery carrier, it is not only able to deliver drugs to the target site effectively, but also should have good safety itself. Toxicity was determined as described herein.

Body Weight Examinations

For determining toxicity of administered minocycline, non-targeted MANP and targeted tfMANP; the gross observable body weight examinations, and histological evaluation were performed. Before treatment, body weight was determined for all the animals. During the course of observation period of 35 days, the animals were followed up twice daily for symptoms of any adverse effect and were physically examined for the sign of morbidity throughout the study period.

The administration of minocycline, non-targeted MANP and targeted tfMANP was discontinued after observing if a single adverse behavioral change like shivering, changes in awareness, motor activity, and touch response. On day 0, 15 and 35, all the animals were weighed, and their weights were recorded.

Gross Observable Behavioral Effects

The procedures devised by Irwin (1968) were followed and the gross observable effects of minocycline, non-targeted MANP and targeted tfMANP were compared. The animals were observed for a period of 35 days for their behavioral reactions. Animals under study were examined for adverse effect symptoms, like change in body weight, stool, condition of eyes, and nose.

Beside the above features monitored, the general signs like writhing, color of skin and mucus membrane were also investigated for any changes during treatment.

Hematoxylin and Eosin (H&E) Staining

Histological examination was adopted to demonstrate the toxicity of minocycline, non-targeted MANP and targeted tfMANP to main organs. Rats were perfused with buffered (0.4 M phosphate buffer, pH 7.6) 4% paraformaldehyde. The brain, liver, lungs, kidneys, and spleen were removed from each animal and immersion-fixed in the same fixative for 24 h at room temperature. The tissues were embedded in OCT, followed by cryostat sectioned. Hematoxylin and eosin (H&E) were used to stain the sections and the slides were observed by optical microscope to further investigate the potential signs of toxicity (i.e., cellular shrinkage, lesion or blebbing, steatosis in liver cells, condensation of chromatin, rupture of cell membrane and apoptotic bodies).

During drug prevention and treatment of hearing loss, the BBB/BLB limits the effective delivery and efficacy of therapeutic drugs in the inner ear. The disclosed minocycline-loaded targeted and stealth PEGylated albumin nanoparticle delivery systems improve the ability of drugs to cross the BBB and BLB, and provide continuous improvements in treatment of hearing loss. A blast induced hearing loss model was created and results of ABR testing observed. The blast setup induced for these studies produced reproducible blast overpressures and physiological and physical damage to the auditory system of rats. The present disclosure demonstrates that free minocycline and its loaded PEGylated nanoparticle displayed greatly and enhanced the protective efficacy in bTBI induced hearing loss after systemic application through central auditory system. Minocycline and the present disclosed nano-formulation is applicable to the treatment of a variety of inner ear disorders. Depending on the embodiment, a combination effect of nano formulation with aminoglycoside antibiotics, and minocycline for bacterial infection could also be a means of ameliorating ototoxic hearing loss.

The above objects and advantages are met by the present invention. In addition, the above and yet other objects and advantages of the present invention will become apparent from the hereinafter set forth. Brief Description of the Drawings, Detailed Description of the Invention and claims appended herewith. These features and other features are described and shown in the following drawings and detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that those having ordinary skill in the art will have a better understanding of how to make and use the disclosed composition and methods, reference is made to the accompanying figures wherein:

FIGS. 1A-1B are schematics of one embodiment of the proposed formulation and strategy, FIG. 1A showing Scheme for formulation of minocycline loaded tfr targeted albumin nanoparticle (tf conjugated MANP) (tfMANP) characterization and its biodistribution analysis; FIG. 1B showing a schematic of ligand conjugated minocycline loaded albumin nanoparticle (mDTANP);

FIG. 2A is a freeze dried sample of (a) MANP and FIG. 2B is a freeze dried sample of (b) tfMANP; FIG. 2C shows particle size of (c) MANP and FIG. 2D shows the particle size of (d) tfMANP; FIG. 2E is a representative SEM image for (e) MANP (magnification=25,000×) and FIG. 2F is a representative SEM image for (f) tfMANP (magnification=30,000×); FIG. 2G is a representative TEM image for (g) MANP (magnification=26,000×) and FIG. 2H is a representative TEM image for (h) tfMANP (magnification=26,000×), with FIGS. 2A-2H having particle size, PDI, zeta potential and Entrapment Efficiency Data expressed as mean±SD (n=3), statistical significance (p<0.05), PDI: Polydispersity Index; FIG. I is a representative summary table showing particle size, PDI Zeta potential, and Entrapment Efficiency;

FIGS. 4A-4C are graphical representations of a chromatogram of FIG. 4A a) supernatant from blank nanoparticles; FIG. 4B b) minocycline standard solution (150 µg/mL); and FIG. 4C c) supernatant from nanoparticles (minocycline sample, 100 µg/mL);

FIGS. 5A-5B are graphs, FIG. 5A is a graphical representation of a drug release profile of a minocycline loaded albumin nanoparticle, values shown here represent SD (n=3), two-way analysis of variance (Anova), and multiple comparison analysis ***P<0.001; FIG. 5B, circular dichroism spectra of BSA, tfMANP and cy5.5 tagged MANP at 500 µg/mL in PBS; further, a circular dichroism was used to elucidate the possible structural changes including local conformational changes and rigidity of the residues of BSA, tfMANP and cy5.5 tagged MANP; these secondary interactions were stable upon ethanol desolvation, glutaraldehyde cross linking and ligand conjugation process; FIG. 5B also illustrates a formulated tfMANP and cy5.5 tagged MANP displayed good colloidal stability and typical patterns of BSA and tfMANP circular dichroism spectroscopic analysis;

FIGS. 6A-6B are bar charts showing stability analysis minocycline loaded albumin nanoparticle by measuring change in particle size and PDI of lyophilized powder stored at either 4° C. or 25° C., over a 3-month time period, wherein values shown here represent SD (n=3), and two-way Anova, multiple comparison analysis ***P<0.001;

FIGS. 7A-7E are photographs and graphs showing FIG. 7A (A) a photo of the 9-inch square cross section, 22 ft long shock tube instrumented with pressure sensors, FIG. 7B (B) an aerodynamic rat holder mounted in the test section (top), with rat placed on top (middle) and animal wrapped in a harness to minimize head and body motion during blast exposure (bottom), FIG. 7C (C) a representative overpressure profiles as measured in the test section at the location of the animal's head for 10 experimental groups used in the present study, FIG. 7D (D) a logistic regression dose-response model for rats exposed to single blast with intensity in the range of 60-450 kPa peak overpressure (left) and corresponding impulse (90-780 Pa·s right). Different levels of injury severities are determined based on survival, and FIG. 7E (E) a setup for behavioral study of anxiety and memory;

FIG. 8B (b) Biodistribution of minocycline and targeted nanoparticle in moderate blast TBI rat model; Two-way Anova, Multiple comparison analysis ***P<0.001; FIG. 8C (c) Schematic of Nanoparticle localization experiment; FIG. 8D (d) Nanoparticles internalized in brain parenchyma and glial cells by crossing the BBB and active targeting via transferrin receptors; bTBI rats were intravenously injected with Cy5.5 conjugated MANP and tfMANP and then sacrificed 6 h after the injection; Brain tissues were collected from 6 h after injections of Cy5.5 conjugated MANP and tfMANP; Sections were observed under a confocal microscope; The distribution in brain parenchyma and uptake of Cy5.5 conjugated MANP and tfMANP (white) by microglia and astrocytes is shown; Scale bar=100 µm;

FIG. 9B (b) Novel object recognition test for minocycline, tMANP and MANP treated moderate bTBI rat model (n=5);

FIG. 11B (b) Mean ABR thresholds and shifts after blast TBI in rat model at acute and chronic conditions. The rats were treated with sham, blast, minocycline, non-targeted MANP and targeted tfMANP group. Error bars represent SEMs. *P<0.05;

FIGS. 12A-12B are line graphs showing calibration curves for minocycline standard solution (0-200 µg/mL), wherein FIG. 12A is a) calibration curve of minocycline individual run and FIG. 12B is b) calibration curve of minocycline combined run (n=3);

FIGS. 13A-13C are graphs showing a chromatogram of minocycline analyzed with varying flow rate of mobile phase 0.02% formic acid in water to acetonitrile (75:25), wherein FIG. 13A is a) 0.75 ml/min; retention time 2.6 min, FIG. 13B is b) 0.5 ml/min retention time 3.96 min, and FIG. 13C is c) 0.25 ml/min; retention time 7.98 min;

FIGS. 14A-14C are graphs showing a chromatogram of minocycline analyzed with varying mobile phase (0.02% formic acid in water to acetonitrile) ratio with flow rate of 1 ml/min wherein FIG. 14A is a) 50:50 mobile phase ratio; retention time 1.33 min, FIG. 14B is b) 50:50 mobile phase ratio; retention time 1.29 min; and FIG. 14C is c) 50:50 mobile phase ratio; retention time 1.78 min;

FIGS. 15A-15D are graphs showing a Chromatogram of minocycline treated with FIG. 15A showing a) 1M sodium hydroxide; peak 1 degradant (1.42 min); peak 2 degradant (1.58 min); FIG. 15B showing b) 1 N Hydrochloric acid, peak 1 degradant (1.42 min); peak 2 Minocycline (2.036 min), FIG. 15C showing c) Hydrogen peroxide peak 1 degradant (1.53 min); and FIG. 15D showing d) light exposure Peak 1 Minocycline (2.15 min);

FIG. 16 is a table showing robustness of the HPLC method to determine minocycline (n=3);

FIG. 17A is (a) histopathological evaluation of the major organs of rats treated with physiological saline, minocycline, non-targeted MANP and targeted tfMANP; histological analysis of the organs (liver, kidneys, lungs, and spleen) compared to the control group; no abnormal histopathological findings were observed in liver, kidneys, lungs, and spleen; FIG. 17B is (b) Body weight changes in blast TBI rats treated with physiological saline, blast, minocycline, non-targeted MANP and targeted tfMANP. Values are mean±SD (n=3) and have been analyzed using one-way ANOVA; data revealed significant ***p<0.001; after 15 and 45 days increase in the body weight in all treated groups as compared to the control group;

in FIG. 18B is an aerodynamic rat holder mounted in the test section (top), with rat placed on top (middle) and animal wrapped in a harness to minimize head and body motion during blast exposure (bottom); in FIG. 18C is representative of moderate blast overpressure profiles as measured in the test section at the location of the animal's head for 10 experimental groups used in the present study; in FIG. 18D subsequent blast mediated tympanic membrane and central auditory system (CAS) damage; in FIG. 18E free minocycline and its nanoparticle iv administration in bTBI induced rat hearing loss model;

FIG. 19B is representative of tympanic membrane images by otoscope with different conditions;

FIG. 20A illustrates auditory cortex (AC) and FIG. 20B illustrates inferior colliculus (IC) are showing a differential degree of staining n=5. *p<0.05. Scale bar=30 µm;

FIG. 21A illustrates auditory cortex (AC) and FIG. 21B illustrates inferior colliculus (IC) are showing a differential degree of staining n=5. *p<0.05. Scale bar=30 µm;

FIG. 22A illustrates auditory cortex (AC) and FIG. 22B illustrates inferior colliculus (IC) are showing a differential degree of staining n=5. *p<0.05. Scale bar=30 µm; FIG. 23A illustrates auditory cortex (AC) and FIG. 23B illustrates inferior colliculus (IC) are showing a differential degree of staining n=5. *p<0.05. Scale bar=30 µm.

DETAILED DESCRIPTION

Figures 2A, 2B, 2C, 2D, 2E, 2F, 2G, 2H, 2I:
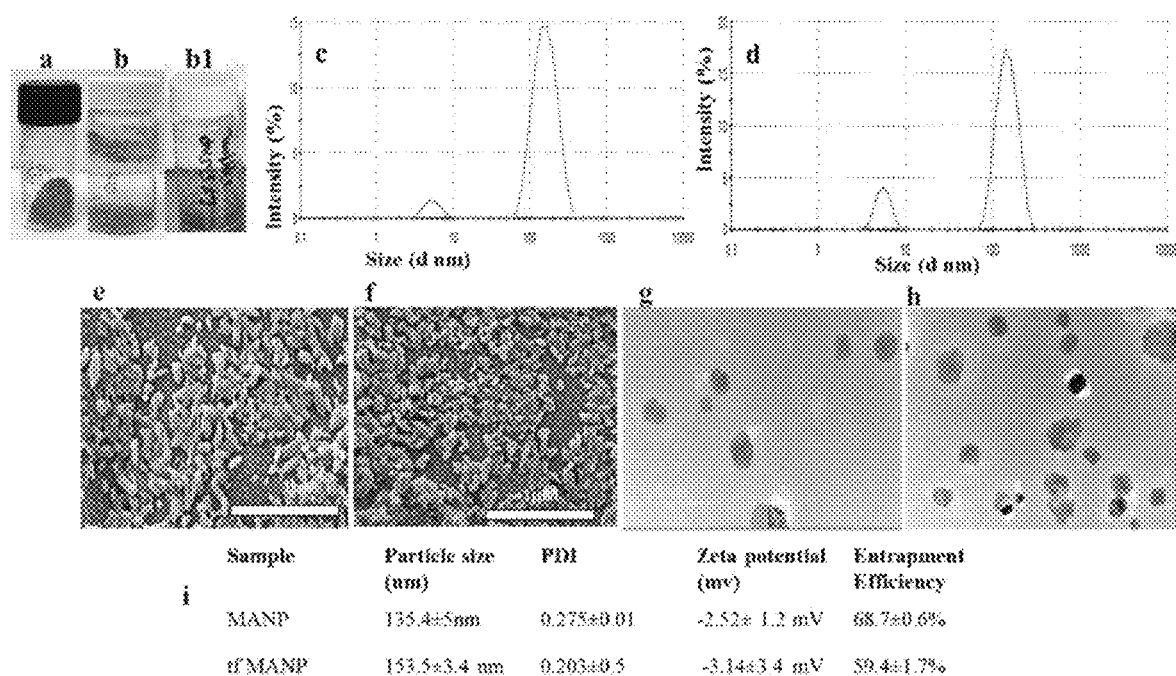
FIGS. 2A-2I are photomicrographs and graphs showing characterization of the physical and chemical properties of MANP and tfMANP.

The present disclosure is directed to a new composition, a process, and novel strategy for a targeted drug delivery approach in treating central nervous system injury, including traumatic brain injury (TBI), by administering a subject with nanoparticle-based minocycline formulations. The novel formulation contains nanoparticles encapsulating minocycline for neuroprotective effect in TBI. Provided are nanoparticle-based minocycline formulations for enhanced delivery to brain, and reduced toxicity at minimal dosage for treating a subject suffering from central nervous system injury including, but not limited to, blast induced traumatic brain injury (bTBI). Applications for other diseases that affects the brain may also benefit from this new treatment.

Though basic construct of minocycline loaded targeted albumin nanoparticle is an unforeseen modification of prior attempts of a formulation of albumin based targeted nanoparticle, its enhanced brain delivery and subsequent therapeutic application in moderate blast TBI model is a novel study (as indicated in FIGS. 1A-1B). It was found by the present investigators that nanoparticle administered at minimal dose in rat blast TBI model, exhibited the BBB crossing and enhanced therapeutic concentration compared to free minocycline. Again, to the best of the present investigator's knowledge, there has been no report on formulation, characterization and therapeutic effect of minocycline loaded albumin nanoparticles in moderate bTBI model. Therapeutic effect of free minocycline was also not explored in moderate bTBI model. Further, the same nanoparticle structure can also be applied in other neurological conditions including traumatic brain injury, Parkinson's diseases, Alzheimer's disease, brain HIV, cancer, and the like.

In the past, nanoparticles made of human serum albumin (HSA) and/or minocycline were prepared using a desolvation technique. Briefly, 200 mg of HSA was dissolved in 2 ml of a 10 mmol NaCl solution. The pH was adjusted to 8.0 by addition of 0.1 N NaOH. 8 ml of ethanol 96% were added with a speed of 1 ml/min under stirring to form the nanoparticles. To stabilize the colloid, the particles were then cross linked with 200% glutaraldehyde (235 µl of an 8% solution) relative to the free amino groups of HSA (=100%). The particles were purified by threefold centrifugation (8 min at 16100 g) and redispersion in ultrapure water. The purified particles had an average diameter of 199 nm measured by dynamic light scattering. Apo E was attached to the surface of these particles via a bifunctional Mal-PEGNHS crosslinker which reacts with an amino group on the particle's surface as well as a thiol group introduced into the Apo E and therefore links the two reaction partners covalently. These findings indicate that nanoparticles with covalently bound apolipoprotein E are taken up into the cerebral endothelium by an endocytic mechanism followed by transcytosis into brain parenchyma.

Apolipoprotein E bound loperamide-loaded HSA-NP (albumin) preparation induced antinociceptive effects in the tail-flick test in ICR mice after intravenous (i.v.) injection. Prior results indicate that apolipoprotein E attached to the surface of nanoparticles facilitates transport of drugs across the blood brain barrier, probably after interaction with lipoprotein receptors on the brain capillary endothelial cell membranes. Another investigating team, Karsten Ulbrich et al, manufactured Human serum albumin (HSA) nanoparticles by desolvation. Transferrin or transferrin receptor monoclonal antibodies (OX26 or R17217) were covalently coupled to the HSA nanoparticles using the NHS-PEG-MAL-5000 crosslinker. Loperamide was used as a model drug since it normally does not cross the blood-brain barrier (BBB) and was bound to the nanoparticles by adsorption. Loperamide loaded HSA nanoparticles with covalently bound transferrin or the 0×26 or R17217 antibodies induced significant anti-nociceptive effects in the tail-flick test in ICR (CD-1) mice after intravenous injection, demonstrating that transferrin or these antibodies covalently coupled to HSA nanoparticles are able to transport loperamide and possibly other drugs across the BBB.

The present investigators made major modifications and a novel nanoparticle from existing technologies. Achieved by the present investigators was loading of minocycline in albumin nanoparticles (no literature report is existing). Further the novelty of the invention also includes evaluation of free minocycline free molecule and minocycline loaded albumin nanoparticle (MANP) and targeted MANP (tf-MANP) in moderate blast TBI in vivo model for neuroprotective effect, in terms of behavioral, pathological, and biochemical analysis (no literature report is existing). Further toxicity of the minocycline was also evaluated in vivo comparing both free minocycline and nanoparticle version.

For the modification of targeted nanoparticle (MANP), exploited is both receptor-mediated endocytosis in vasculature and glial cells; and transiently leaky BBB to enhance the bioavailability at injury site and reduce the toxicity of the drug. Literature also reported that loperamide loaded albumin nanoparticles with covalently bound transferrin or the 0×26 or R17217 antibodies was capable of transporting loperamide across the BBB and induced significant anti-nociceptive effects. Antibodies to the integrin receptor CD11b, also known as complement receptor 3 (CR3), have the potential to be used for targeting immunogenes to microglia.

Tf conjugated BSA Nanoparticle was formulated in three steps. In the first step, minocycline loaded albumin nanoparticle (MANP) was prepared using a modified desolvation method. Briefly, 10% BSA (w/v) in HPLC grade water was stirred (at 600 rpm) with 7.5% of minocycline (w/v) at room temperature for drug absorption onto albumin. After 1 h of continuous stirring, the pH value was adjusted from 7.5 to 9 using 0.1 M NaOH. The mixture was then desolvated through addition of a suitable amount of ethanol, using a peristaltic pump at a rate of 1 ml/min under stirring (at 600 rpm). Ethanol addition was sustained till turbidity point and residual ethanol was removed by a rotary evaporator at 4° C. Then, the formulated minocycline-loaded nanoparticle was stabilized by crosslinking with 8% glutaraldehyde solution for 24 hr. The nanoparticle in solution was ultra-centrifuged (Sorvall LYNX 6000, Superspeed Centrifuges) at 36288 g force for 40 min.

Secondly, 2-iminothiolane solution was added to bind a sulfhydryl group to the transferrin, and was quantified through use of Ellman's reagent. Briefly, transferrin was dissolved in phosphate buffer (1 mg/ml at pH 8.0) and incubated with 12.8 µl (50.85-fold molar excess) of 2-iminothiolanesolution (6.9 mg in 1.0 ml phosphate buffer, pH 8.0) in the dark for 2 h at 20° C. under constant shaking (500 rpm). Thereafter, the thiolated transferrin was purified by PD-10 Columns Sephadex™ G-25 M, using phosphate buffer (pH 8.0) as eluent.

Thirdly, NHS-PEG-MAL-5000 solution in 10-fold molar excess was introduced to the nanoparticles to cross-link activate them. To conjugate the NPs, 500 µl of thiolated and purified transferrin solution was added to 500 µl of reactive BSA NPs. The mixture was incubated under shaking for 24 h at room temperature. Thiolated transferrin excess was removed by 2-fold nanoparticle centrifugation, redispersed in water and lyophilized. Precipitate obtained from the centrifugation was washed with pure water three times and then freeze dried to obtain brownish fine powder of Tf conjugated MANP. For further characterization, a stock suspension of NP was used. Similarly, the drug free ligand conjugated empty albumin nanoparticle (tfEANP) was also prepared.

Two separate approach was utilized to redisperse the lyophilized MANP, physical shaking and sonication. Manually shaking method was applied using weighed quantity of lyophilized NP with phosphate buffer saline pH 7.4. The nanosuspension was subject to gentle shaking for 2 min to redisperse the solution and then immediately measured for particle size using a Malvern zeta sizer. After gentle shaking for 2 min the nanosuspension was subjected to particle size measurement using Malvern zeta sizer. Micrometer sized particles were considered non-dispersible. Sonication method was applied with lyophilized NP in phosphate buffer saline pH 7.4 for 2 min using a bath sonicator and redispersibility.

As discussed, in central nervous system (CNS) disorders especially neurodegenerative disorders are the major challenge for public health and demand the great attention of researchers to protect people against them. In past few decades, different treatment strategies have been adopted, but their therapeutic efficacy are not enough and have only shown partial mitigation of symptoms. Blood-brain barrier (BBB) and blood-cerebrospinal fluid barrier (BSCFB) guard the CNS from harmful substances and pose as the major challenges in delivering drugs into CNS for treatment of CNS complications nanotechnology has come out as an exciting and promising new platform of treating neurological disorders and has shown great potential to overcome problems related to the conventional treatment approaches.

The present investigator's targeted minocycline nanoparticle effectively penetrates the BBB, and exhibit anti-inflammatory and neuroprotective effects to benefit TBI patients with minimal or no toxicity at low dose and reduced frequency of dose administration. Due to the versatility of the present invention's delivery system, it can also cargo other therapeutic molecules and be applied for the diagnosis and treatment of various CNS diseases conditions Alzheimer's disease (AD), Parkinson's disease (PD), Huntington's disease (HD), stroke, epilepsy, brain tumors, multiple sclerosis (MS), and encephalitis.

The objective of the present study was to formulate and characterize tf-conjugated minocycline-loaded bovine serum albumin (BSA) based nanoparticles and perform an in vivo biodistribution study in rat TBI model for potential application in brain injury. In the present study, BSA was used as the nanocarrier as it possess high stability and antigenicity with low toxicity and immunogenicity.

To the best of the present investigator's knowledge, this is the first study to report a novel tf (transferrin) conjugated albumin-based nanoparticles formulation in rat TBI model to achieve enhanced brain delivery of minocycline at reduced dose. Further in vivo biodistribution in rat TBI model was also studied to validate the enhanced bioavailability of minocycline in brain (as shown in FIG. 1A).

Widely-acknowledged barriers such as the BBB and the extracellular space of brain parenchyma known for preventing nanoparticles (NPs) from reaching the targeting site. If the NPs unselectively distribute in the whole brain, the improvement of treatment outcome caused by elevated drug concentration might accompany even worse side effect to CNS. Hence, the targeting approach using nanoparticle is highly essential for initially to transport nano-cargo across the BBB and subsequently to target specific cell in injured brain region. A number of dual ligand targeted delivery approach has been explored for treatment of various brain disorders. Noted examples are (1) In a HIV model, the dual-antibody-modified chitosan/small interfering RNA (siRNA) nanoparticles to deliver siRNA across the blood brain barrier (BBB) and then targeting HIV-infected brain astrocytes was studied. (2) Analgesic effect on CNS was studied using human serum albumin nanoparticles (HSA NPs) coupled to transferrin or TfR-mAb displayed a significant loperamide transport across the BBB into the brain and CNS analgesic effect. (3) Combination of a folate receptor (tumor cells) and a TfR (BBB endothelial cell), or a TAT receptor (tumor cells) and a transferrin receptor (TfR, BBB endothelial cells), both demonstrated the increased brain tumor uptake of therapeutics in vitro and extended survival compared to single targeting therapy. (4) Angiopep-2 and EGFP-EGF1 dual modified nanoparticle for specifically targeting neuroglial cells in normal brain because the low-density lipoprotein receptor-related protein (LRP) (receptor of angiopep-) is overexpressed on the BBB.

The present modification of dual targeted nanoparticle (tfMANP) exploits both receptor-mediated endocytosis in vasculature and glial cells; and transiently leaky BBB to enhance the bioavailability at injury site and reduce the toxicity of the drug (FIG. 1A and FIG. 1B). Literature also reported that loperamide loaded albumin nanoparticles with covalently bound transferrin or the OX26 or R17217 antibodies was capable of transporting loperamide across the BBB and induced significant anti-nociceptive effects. Antibodies to the integrin receptor CD11b, also known as complement receptor 3 (CR3), have the potential to be used for targeting immunogens to microglia. The present investigators have synthesized albumin nanoparticle (tf MANP) conjugated with dual ligands (Tf ligand and CD11b antibody) to target brain endothelial (transferrin receptor) and glial cells (CD11b antigen), respectively.

Based on the preliminary studies and existing reports, it was determined that ligand functionalized albumin nanoparticle enhances bioavailability of minocycline at brain parenchyma and glial cells at minimal dose and frequency (than currently administered multiple doses of high concentration of minocycline), ameliorating chronic inflammation and preventing secondary neuronal injury. The major focus of the suggested modification is to provide the needed bioavailability/cell targeting in the injured brain at significantly lower dose so as to achieve maximum bioavailability of minocycline through a novel tfMANP. Through this study, it is confirmed that the tfMANP at minimal dosage is capable of accumulating in parenchyma/glial cell and attaining pharmacological neuroprotective concentration. Further, tfMANP formulation is superior in terms of neuroprotective effects in TBI model with minimal or no toxicity in comparison to tfMANP and free minocycline was established. These innovative method of engineering the nanoparticle as well as the expertise of the team assembled will open new ways of delivering a low dose of neuroprotective drugs and other drugs for enhanced therapeutic effect in various CNS conditions including TBI, with minimal or no toxicity.

In one embodiment, the formulations of MANP, tfMANP, and tfMANP are prepared using the following steps. Depending on the implementation, a minocycline loaded albumin-based nanoparticle (tfMANP) can be formulated by a three step method. In the first step an unmodified MANP is produced by a previously described desolvation technique17]. Briefly, BSA will be dissolved in sodium chloride solution, incubated with minocycline and the pH will be adjusted to 9. For the formation of nanoparticles, ethanol will be added with a peristaltic pump at 1 ml/min under stirring. Then the nanoparticles will be cross-linked with glutaraldehyde, purified by 3-fold centrifugation, and redispersed by ultrasonication.

In the second step, sulfhydryl groups is introduced to the tf-transferrin or to the CD11b antibodies by the reaction of the amino groups with 2-iminothiolane, and the amount of the Introduced sulfhydryl groups will be determined with Ellman's reagent.

In the third step, the nanoparticles are activated with the heterobifunctional crosslinker NHS-PEG-MAL-5000 using a 10-fold molar excess and the sulfhydryl-reactive (TO was covalently coupled to the nanoparticles to obtain tfMANP. For co-localization study, cy5.5 is conjugated to the nanoparticle.

Experimental Examples

The following experimental examples are given to merely illustrate the features of the present invention and are in no way meant to limit the scope of the invention to any particular embodiment.

The protein NPs was obtained by desolvation that can be achieved through precise addition of a desolvating agent (ethanol or acetone) to albumin solution at an optimum pH (optimal size and encapsulation) with constant stirring until turbidity. A decrease in the solubility of albumin followed by phase separation in water during the desolvation process leads to nanoparticle formation. Further, the nanoparticles can be stabilized by crosslinking lysine and guanidino side chains of albumin with the crosslinking agent glutaraldehyde. When crosslinking is increased, the rigidity of the nanoparticle can lead to successive decreases in particle size due to the formation of more compact particles.

In the present experiment, hydrophobic minocycline aggregates in aqueous solution and interacts with the hydrophobic regions of the BSA forming nanoparticle, which was stabilized with glutaraldehyde by cross-linking the surface amino groups of BSA. The $NH_2$ from BSA molecule when comes in contact with the carbonyl group of glutaraldehyde, reacts to form the —N=C— bond by losing a molecule of water. In this way the nanoparticles of albumin crosslinked with glutaraldehyde are formed. The glutaraldehyde crosslinked with albumin has no toxicity, and the obtained NPs are non-toxic. However, the free unbound glutaraldehyde may display toxicity. Hence, unreacted glutaraldehyde was removed by centrifugation and purification.

One of the major focuses of the present study is to provide the needed bioavailability/cell targeting in the injured brain at a significantly lower dose to achieve maximum bioavailability of minocycline through a novel MANP. The present research of tfr (transferrin receptor) targeted MANP nanoparticle exploits both receptor-mediated endocytosis in vasculature and transiently leaky BBB to enhance the bioavailability at injury site and reduce the toxicity of the drug.

Minocycline-loaded albumin nanoparticles were freeze dried, resulting in a brownish powder that can also be dispersed in PBS or 0.9% saline solution (FIG. 2A and FIG. 2B). Nanoparticles with uniform size allow increased cellular interaction and possess enhanced toxicity. Hence, the size of the nanoparticles plays a critical role in cell interactions and toxicity. Particle size distribution and mean particle sizes of the nanoparticles were measured by DLS in PBS at pH 7.4. The results show a well dispersed colloidal system of MANP nanoparticles with a mean particle size and polydispersity index of 135.4±5 nm and 0.275±0.01 respectively, with the distribution range of 140-250 nm (FIG. 2C). In the case of ligand conjugated minocycline loaded nanoparticle (tfMANP), it exhibited a mean particle size and polydispersity index of 153.5±3.4 nm and 0.203±0.5 respectively (FIG. 2D). Studies have reported that cellular uptake and cytotoxicity depend on the surface charge of the nanoparticle. Lyophilization may increase the particle size of the nanoparticle, possibly due to aggregation; hence we checked the redispersibility of the particles after lyophilization using mechanical shaking and bath sonication methods.

Morphological analysis of freeze-dried MANP and tfMANP sample was carried out with FE-SEM, and the images obtained are shown in FIG. 2E and FIG. 2F. Both types of synthesized NPs had an approximately spherical morphology with, and some extent connected to each other and an average size of 120±30 nm for MANP and 148±6 nm for tfMANP synthesized at pH 7. Furthermore, tfMANP showed a majorly uniform distribution, minimally differing in size when compared to MANP. TEM analysis showed that MANP and tfMANP samples have a spherical and similar in size range, measuring 120-180 nm in diameter (FIG. 2G and FIG. 2H) compared to SEM and zetasizer analysis. The zeta potential quantifies the degree of repulsive interaction between nanoparticles and depends on the concentration of polymer and the incorporated drug. Specifically, zeta potential is calculated as the difference in electrical potential between the surface of the nanoparticle and the bulk-surrounding medium. Zeta potential information is helpful in predicting the storage stability of colloidal dispersions. In the present study, MANP and tfMANP exhibited an anionic charge of −2.52±1.2 mV and −3.14±3.4 mV respectively. Albumin comprises free carboxyl and amine groups, both of which could be utilized for covalent modification. In general, albumin shows a negative zeta potential (high anionic) at the physiological pH and saline. Further, negative albumin (nearly neutral) can also be obtained with surface modification with anionic groups.

Minocycline-Loaded Albumin Nanoparticles (M-ANP)

The present formulation of minocycline-loaded albumin nanoparticles (M-ANP) is based on the modified desolvation method. Many studies have reported albumin-based drug-loaded nanocarriers with chemical crosslinking agents such as glutaraldehyde.

In the present study, parameters such as the pH level (between 7.0-9.0), and the amount of ethanol added were varied to optimize particle size. Table 1). Though the initial particle size was at a higher range (>275 nm), by the end of the ethanol addition, the particle size stabilized and became reproducible after glutaraldehyde cross linking, rotary evaporation of ethanol and lyophilization process. In addition, at 10% w/v BSA and 1:1.3 addition of BSA to ethanol, maximum yield of 68.9% was obtained. Particle sizes were higher when pH was <7.0 but pH level between 7.0-9.0 produced uniformly sized albumin nanoparticles. Further, when the ratio of BSA to ethanol was 1:2.5, the yield was higher than 1:5 ratio. Subsequently, at 1:2.5 ratio of BSA to ethanol, the particle size also increased to 320 nm, which was prior to the ethanol removal. Upon ethanol removal and lyophilization, the particle size was reduced to the optimal size and the PDI indicated a nearly homogenized nanoparticle system.

Figure 3:
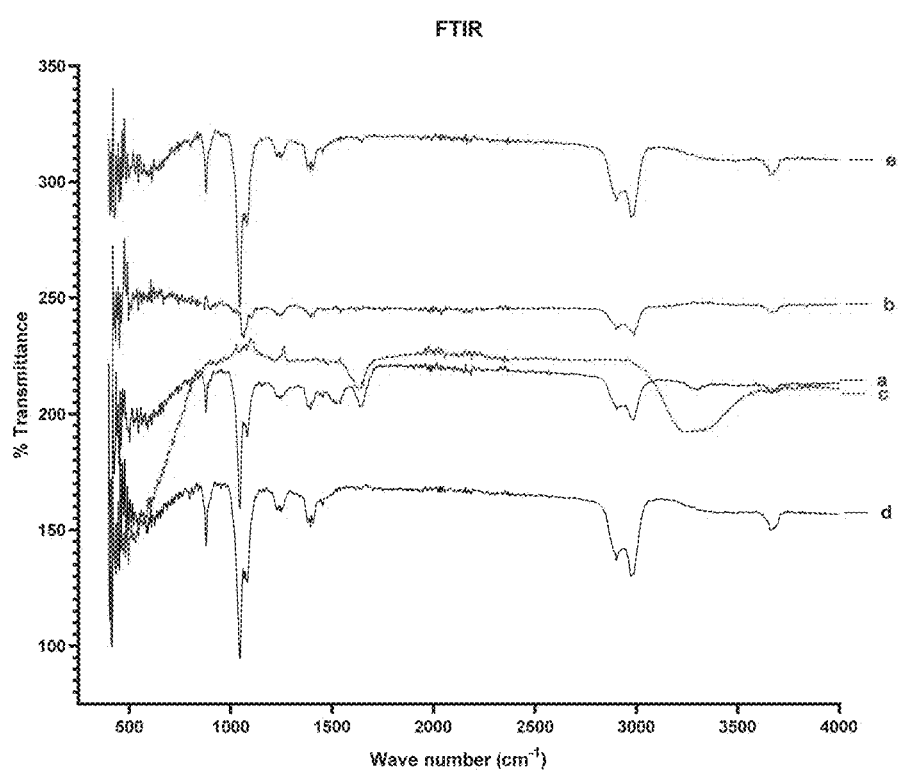
FIG. 3 is a graphical illustration of FTIR spectra wherein the lines are defined as (a) BSA, (b) Transferrin (c) minocycline, (d) MANP and (e) tfMANP due to C—O stretching vibrations, and MANP and tfMANP are showed characteristic bands at 3466 and 1653 cm$^{-1}$ related to O—H alcohol and C=O groups of acids, and the results show the absence of a chemical reaction between BSA and minocycline, suggesting that nanoparticle formation does not modify the chemical structure of the drug, and the presence of the relevant peaks in each nanoparticle confirmed that the minocycline was encapsulated in the BSA nanoparticles.

The present investigators obtained the FTIR spectra of BSA, Transferrin, minocycline, MANP and tfMANP (FIG. 3). The FTIR spectra of BSA displayed several distinguishing peaks at 3319 $cm^{-1}$ arising from amine groups (N—H stretching vibration); a peak of amide bond at 1659 $cm^1$ attributed to C=O stretching vibration (amide I band) and to a mixed vibration of N—H bending and C—N stretching (amide II band) at 1533 $cm^{-1}$. Minocycline exhibited characteristic bands at 3487 $cm^{-1}$. The additional bands at 1597 and 1473 $cm^{-1}$ are due to structural vibrations of benzene rings. The absorption band at 1042 $cm^{-1}$ was due to C—O stretching vibrations. MANP and tfMANP showed characteristic bands at 3466 and 1653 $cm^{-1}$ related to O—H alcohol and C=O groups of acids. The results show the absence of a chemical reaction between BSA and minocycline, suggesting that nanoparticle formation does not modify the chemical structure of the drug. The presence of the relevant peaks in each nanoparticle confirmed that the minocycline was encapsulated in the BSA nanoparticles.

The attachment of Tf molecules to the MANP nanoparticles via amide bonds was confirmed by FTIR spectroscopy. The FTIR spectrum of pure Tf exhibits two strong bands at 1650 and 1530 $cm^{-1}$ which correspond to amide I and amide II, respectively. After the anchoring of Tf to MANP, a significant decrease in the intensities of these two characteristic protein bands, compared to pure Tf, was observed. It should be noted that the amide II band practically disappeared only for covalent conjugate, during the conjugation step. This disappearance is due to the fact that the N—H groups of protein take part in the formation of the amide bonds between Tf and MANP. Moreover, these bands were shifted towards lower wavenumbers by 20 $cm^{-1}$. These two phenomena confirm the successful covalent anchoring of Tf to —COOH groups of MANP Nps via amide bond.

Table 1. Experimental control factors and fixed parameters in the optimization of minocycline loaded albumin nanoparticles. Fixed parameters are stirring rate 1000 rpm, rate of anti-solvent addition 1 ml/min and cross-linking time. Varying parameters were changing the pH and anti-solvent to solvent ratio. Initial optimization was performed with 10% of BSA in 5 ml HPLC water and 0.25% of Minocycline.

TABLE 1

HPLC Method Validation

| PROPERTY | FORMULATION 1 | FORMULATION 2 | FORMULATION 3 |
|---|---|---|---|
| Minocycline loaded albumin nanoparticle size and PDI | 135.4 ± 5 nm and 0.275 ± 0.01 | 232.5 ± 2 nm and 0.625 ± 0.16 | 256.6 ± 8 nm and 1 ± 0.3 |
| BSA and Minocycline (weight ratio) | 10% BSA and 0.25% Minocycline | 10% BSA and 0.25% Minocycline | 10% BSA and 0.25% Minocycline |
| pH | 7.0 | 8.0 | 9.0 |
| RPM | 1000 | 1000 | 1000 |
| Rate of addition | 1 ml/min | 1 ml/min | 1 ml/min |
| Ethanol to Water | 0.65 | 0.825 | 1.13 |
| Cross linking Time (h) | 24 | 24 | 24 |

The accurate assessment of these parameters is critical given that the nanoparticle must be able to act as a vehicle to carry and transport the drug and produce sustained release of minocycline at the therapeutic target. To accomplish this, a verifiable quantification method needs to be developed to quantify nanoparticle encapsulation. Initial HPLC studies, in reference to previous minocycline quantification in plasma, used a methanol-water mixture. Mobile phases consisting of methanol and water at various ratios were tested to obtain a symmetric peak.

However, a regular and symmetrical minocycline peak was only obtained when using an acetonitrile-water mixture acidified with formic acid 25:75 (v/v), at a flow rate of 1 mL/min, with acquisition parameters of column temperature (25° C.), sample temperature (25° C.), injection volume (10 μL), and wavelength (273 nm).

Figures 12A, 12B:
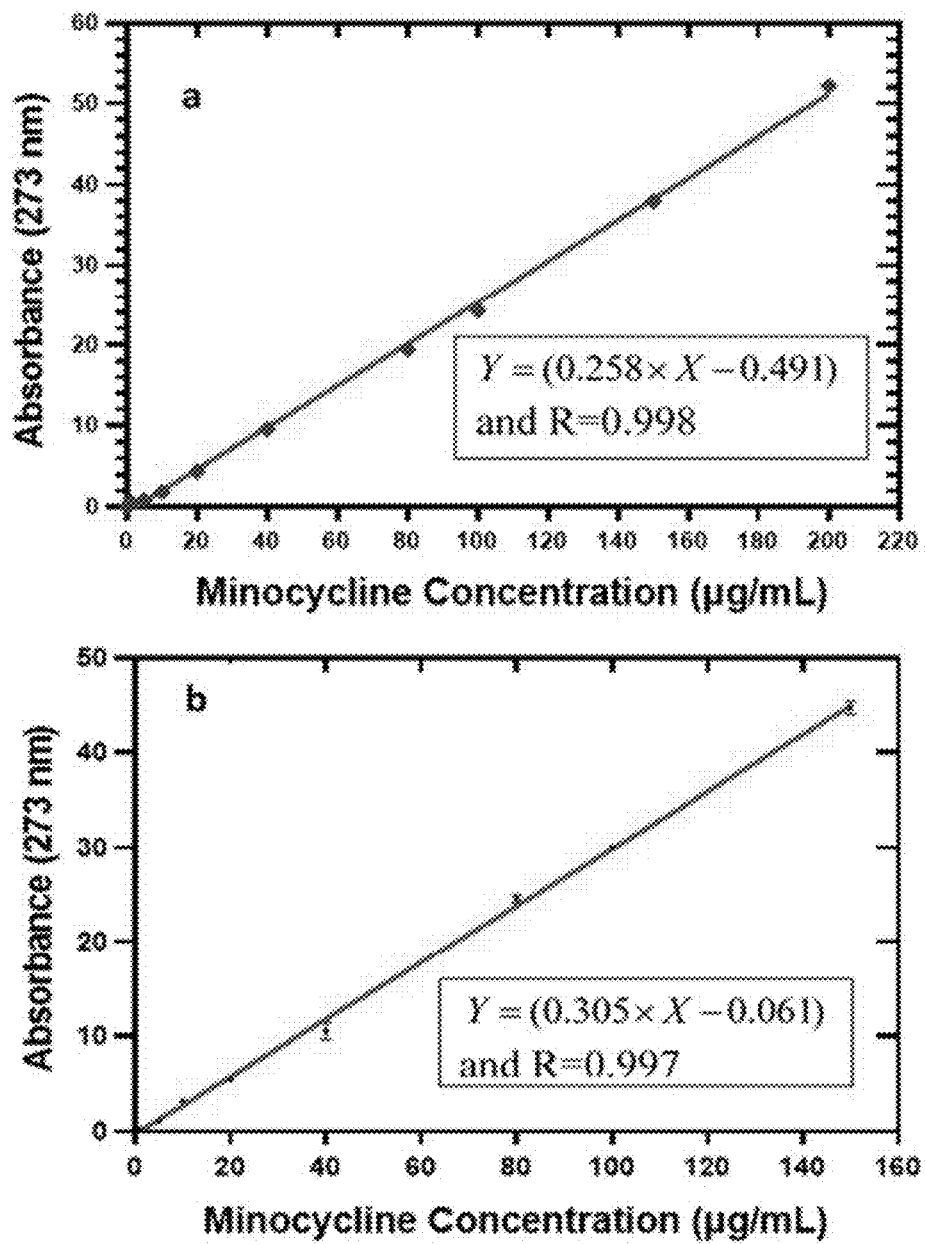

Set to these parameters, minocycline was detected at approximately 1.95 min (FIGS. 4A, 4B, 4C). Suitability of the developed method was calculated as T=1.27±0.04 and N=7535.14±58.3 which matched with the specified limits (T<2; N>2000). Linearity was evaluated at eight concentration levels (0-100 μg/mL) through the method of least squares, resulting in the regression equation Y=(0.258×X−0.491) and correlation coefficient (R=0.998) (FIG. 12A and FIG. 12B).

Specificity of the method was analyzed using the supernatant of the blank, unloaded nanoparticles diluted in acetonitrile. The chromatogram (FIG. 4A) was compared with that of the minocycline sample (FIG. 4C) and the minocycline standard (FIG. 4B). The chromatogram of the supernatant of the blank nanoparticles displayed an additional peak near the retention time, but its small size implies its negligible effect on the quantitative determination of minocycline in nanoparticles (FIG. 4A).

Standard samples were made by spiking the supernatant of blank nanoparticles with minocycline standard solution of varying concentrations and then compared to the corresponding minocycline standard. The recovery of minocycline was nearly 99.8% which indicates that the nanoparticle component from the supernatant showed no interference in relation to the retention time of peak of interest.

Minocycline standard samples (40, 80, and 100 μg/mL) were prepared in triplicate and analyzed on (1) same day (reproducible) and (2) three different days (intermediate precision). The maximum RSD value was mostly below 9.39% indicating the accuracy of the method in Table 2.

TABLE 2

Precision and accuracy of HPLC method to determine Minocycline (n = 3)

| Nominal concentration (μg/mL) | Precision (% RSD) | | Accuracy (% Recovery) | |
|---|---|---|---|---|
| | Intra-day | Inter-day | Intra-day | Inter-day |
| 40 | 1.08 | 17.34 | 111.51 | 81.37 |
| 80 | 2.84 | 5.27 | 112.09 | 106.82 |
| 100 | 7.06 | 9.39 | 109.00 | 100.74 |

*RSD—Relative standard deviation

Table S1 in FIG. 16 describes the percent recovery of the minocycline standard samples for various flow rates and mobile phase ratios. This method was robust in regard to variations in the volumetric ratio of the mobile phase but displayed sensitivity to flow rate modifications (FIGS. 13A, 13B and 13C and FIGS. 14A, 14B and 14C). In the present studies, the minocycline limit of detection and quantification were determined as 125 ng/mL and 250 ng/mL, respectively, which is consistent with previously reported studies in plasma and saliva.

As tetracycline degrades under alkaline pH, chelation, and photo-degradation, minocycline degradation was also analyzed. Chromatograms were obtained for minocycline treated with acid, base, peroxide, and visible light, and all displayed distinct peaks for minocycline accompanied by minor peaks, with the exception of visible light treatment that contained no additional peaks (FIG. 15D).

Specifically, treatment with an acid, base, or $H_2O_2$ induced minocycline degradation, as displayed in FIGS. 15A, 15B, and 15C. Acid degraded minocycline contained an additional peak at a retention time of 1.42 min (FIG. 15B).

With acid and heating conditions, minocycline readily epimerized at the C-4 position of minocycline (two isomers, 4-epiminocycline) and subsequently the degradant was separated in chromatogram.

The present studies results are also consistent with previous reports on minocycline degradation. Similarly, base degraded minocycline exhibited one peak in chromatogram with 1.58 min (FIG. 15A). Minocycline treated with 30% (v/v) $H_2O_2$ showed completely degraded peak at 1.52 min (FIG. 15C) and no minocycline peak was detected. Table 3 details the percent recovery of minocycline when exposed to various degradation conditions.

TABLE 3

Results of minocycline forced degradation (n = 3).

| Exposure Conditions | % Recovery* |
|---|---|
| UV Light | 98.54 ± 0.71 |
| NaOH | 74.05 ± 0.4 |
| HCl | 88.93 ± 0.32 |
| $H_2O_2$ | undetectable |

*The concentration of 100 μg/mL was used.

Acid and base exposure led to minor degradation as the minocycline recovery was 88.93 and 74%. Minocycline showed less degradation when spiked in NaCl medium due to its more acidic pH. Jain et al. also reported that this drug is more susceptible to alkaline than acidic degradation which is consistent with the present investigator's findings.

When minocycline was treated with 30% (v/v) $H_2O_2$, a shift in retention time occurred, rendering percent recovery calculations infeasible and indicating complete minocycline degradation. Exposure of minocycline to visible light did not hamper percent recovery and resulted in a maximum variation of 2%, indicating stability of the drug.

Hence, the developed method is simple, efficient, and sensitive, allowing for the quick analysis of minocycline, and making the method applicable for quantification of minocycline in albumin nanoparticles.

Application of the Developed HPLC Method: Entrapment Efficiency and In Vitro Release Study To develop an optimal drug delivery system, encapsulation efficiency and in vitro drug release are essential parameters to be analyzed. The present formulation of minocycline-loaded albumin nanoparticles is the first to report; there has not been any chromatographic methods to determine minocycline from albumin nanoparticles formulation. In this study, the present investigators have reported that HPLC method is suitable for the quantification of minocycline from a novel albumin nanoparticle.

The encapsulation efficiency of minocycline in the albumin nanoparticles was determined indirectly by centrifuging and collecting the supernatant of the nanoparticles to estimate the free minocycline present in solution. Nearly 59.4±1.7% and 0.45±0.06% of entrapment efficiency and drug loading rate respectively, were determined (n=3). The in vitro release profile of minocycline and minocycline loaded nanoparticle is shown in FIG. 5. At the beginning, burst release of minocycline was observed after 30 min (22.9±1.3%) in dissolution medium in comparison to free minocycline (61.5±2.4%) and gradually an increased release profile was observed until 24 hr.

It is suggested by the present investigators that the surface implanted minocycline would be released earlier than one inside the nanoparticles. In 24 h time duration, approximately 70.3±2.9% of the minocycline was released compared to free minocycline (98.3±1.8%).

Then, the release rate gradually stabilized to a sustained release from 24 h to 72 h, which can be attributed to the soluble nature and formation of interconnected pores on the surface and inside the albumin nanocarrier upon contact with dissolution medium. Further, NPs with glutaraldehyde crosslinking of surface amino groups displayed slower kinetics of drug release.

Stability Study

The size and polydispersity index were measured over a 3-month period using lyophilized minocycline loaded nanoparticle stored at two different conditions (4° C. and 25° C.). Stability of the nanoparticle is shown in FIG. 6A and FIG. 6B.

Freeze dried nanoparticle stored at 25° C. displayed considerable particle size increase. With the particle size attaining approximately 269.2±11.2 nm within 2-months, the system would be considered undesirable for use as a brain targeted drug delivery system in most cases. Minocycline loaded nanoparticles stored at 4° C. were stable with greater uniformity in their particle size measurements during the entire time periods. In the case of PDI values, nanoparticle stored at both conditions of 25° C. and 4° C. exhibited <0.3, in accordance with the acceptable limit for monodispersed nanoparticle distribution. Nonetheless, increases PDI was also observed over the 2-month time period with all conditions except the lyophilized powder at 4° C. Hence, lyophilized nanoparticles stored at 4° C. revealed the supreme stability compared to 25° C. stored nanoparticles conceivably due to aggregation in longer storage.

Therefore, to guarantee nanosized, homogenized particles for subsequent studies, the formulations was prepared fresh as lyophilized powder at 4° C. or prevented from settling by constant gentle mixing prior to use.

Figure 10:
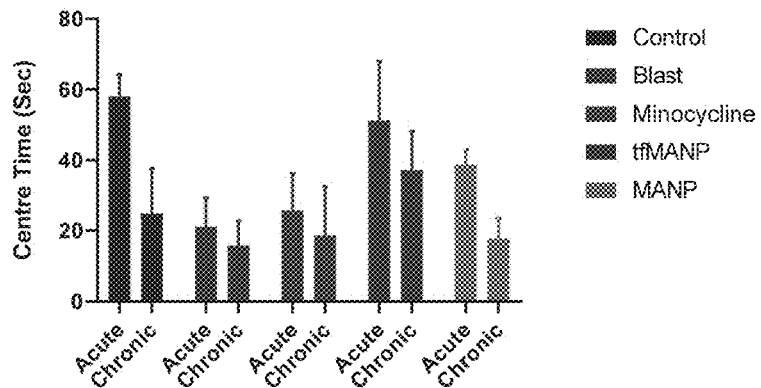
FIG. 10 is a bar graph showing open field Test for minocycline, tMANP and MANP treated moderate bTBI rat model (n=5)

The laboratory at Center for Injury Biomechanics, Materials and Medicine (CIBM3) has a well-validated blast tube, which is capable of accurately delivering shock waves at different intensities. Animal model of blast TBI to represent diffuse brain injuries using shock tubes is shown in FIG. 10. The model is capable of accurately generating shockwaves with different intensities.

Additionally, varying blast overpressures (BOPs) from 35 kPa to 350 kPa and using approximately 650 rats the present studies model we have generated dose-response curves which categorized the injury severity from sub-mild, mild, moderate and severe (FIG. 7C). The BOP we employ in the current study represents moderate injury.

Shock Tube, Dose Response Curve and Behavioural Study Setup:

FIGS. 7A-7E illustrate the setup used during the present investigation.

Enhanced Biodistribution of Nanoparticle/Minocycline in bTBI rat Model will now be discussed in view of the above setup. Bioavailability to the organ of interest is an important criterion since low bioavailability requires the use of excessive dosage, which in turn triggers serious side effects in the central and peripheral systems. Performed in vivo was biodistribution using targeted nanoparticle in rat TBI model. The results showed maximal concentration (~3' higher) of minocycline accumulation in targeted nanoparticle administered group (after 24 hr) compared to free minocycline injection due transferrin (tfr) receptor (BBB) mediated uptake of nanoparticle (conjugated with transferrin ligand) in brain tissue and short half-life of minocycline 2-3 hrs. The brain bioavailability of higher concentration of minocycline for longer time (24 hrs) at single dose of nontoxic concentration (3 mg/kg) of targeted nanoparticle compared to free minocycline administration will serve as a proof-of-concept. This effect may be shown in FIG. 8B.

Both free minocycline and Tf conjugated MANP were compared in terms of biodistribution in different organs using a rat TBI model at 4 hr and 24 hr post-administration. The present study demonstrated that administering the targeted nano-formulation achieved 3-fold more bioavailability as compared to administering free minocycline (FIG. 8). However, the other organs like the liver, spleen and lungs displayed lower minocycline (nanoparticle) distribution as compared to the brain and free minocycline group. This enhanced delivery of minocycline in the brain compared to other organs can mainly be attributed to particle size, surface charge and transferrin (an endogenous ligand for the Tfr receptors present in the BBB), which assisted in increasing the permeability of the nanoparticle into the brain and subsequent interaction with the cell membrane.

It is also possible that the compromised BBB in blast induced brain injury may have also contributed to enhanced delivery of minocycline and targeted MANP. However, it could be seen that the significant difference in minocycline in the brain parenchyma after administration of free minocycline and targeted MANP in rat TBI model. It is also postulated that the P-gp efflux pump located at endothelial cells of the BBB plays a crucial role in the efflux mechanism of the brain. Therefore, minocycline probably effluxes out of the brain.

Accumulation of Nanoparticle Brain Parenchyma In Vivo bTBI Model

The CNS is well protected by the BBB which not only maintains homeostasis but also hampers the systemic delivery of therapeutically important drugs from the blood to the brain. Traditional approaches employed for enhancing drug concentrations in the brain, such as direct intracerebral drug injection or disruption of the BBB, are associated with high risks. Biodegradable polymeric nanoparticles are one of the most promising drug and gene delivery systems that cross the BBB. Nanoparticle formulations can encapsulate molecules with therapeutic value and enhance drug transport through the BBB in patients with ischemic brain injury.

Figures 8A, 8B, 8C, 8D:
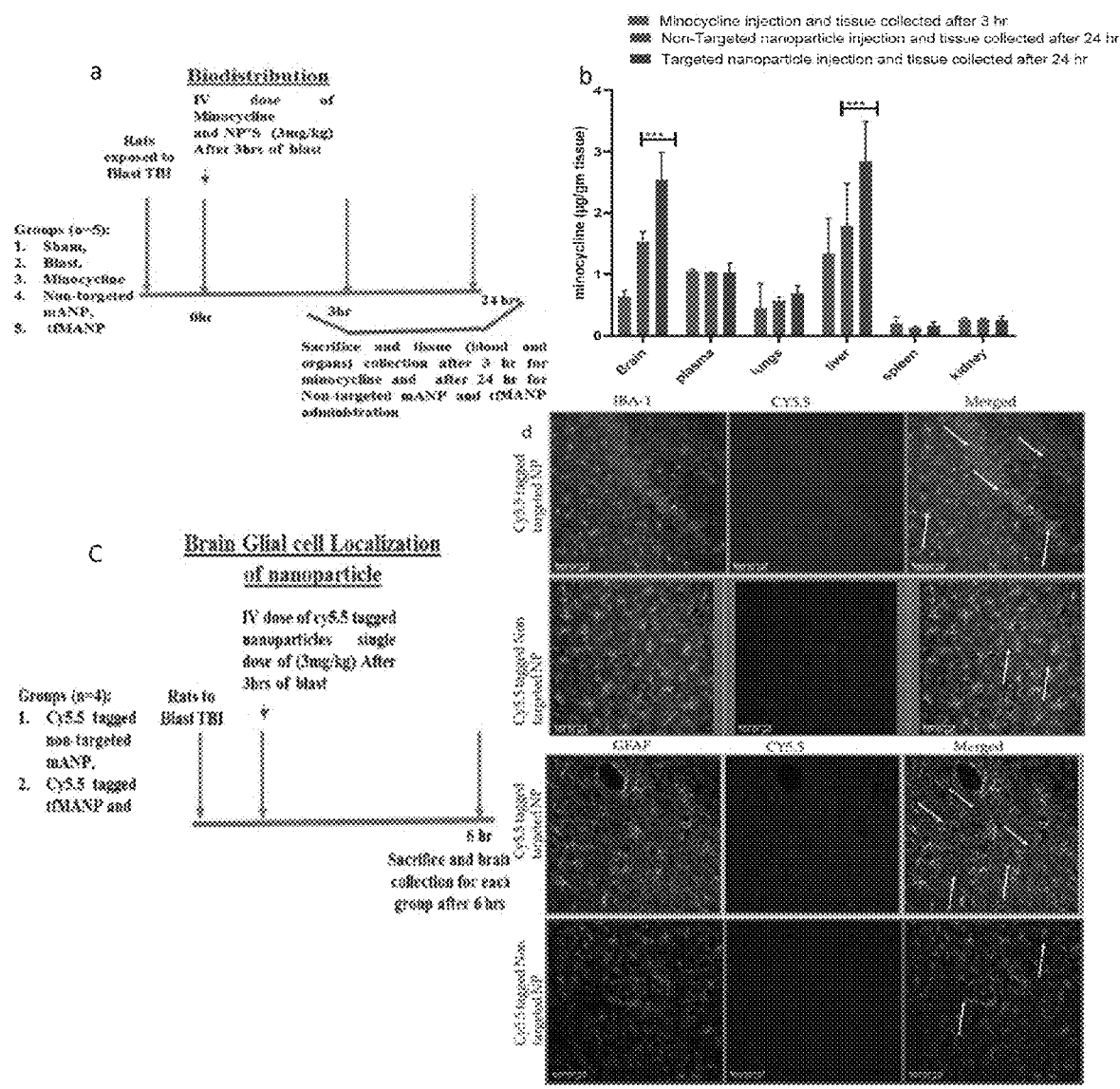
FIGS. 8A-8D FIG. 8A (a) Schematic of biodistribution experiment.

In the present study, it was investigated whether Cy5.5 conjugated MANP and tf-MANP localized after crossing the BBB. With non-targeted MANP and targeted tf-MANP, tissue confocal microscopy was used to observe the distribution of fluorescent signal for a Cy5.5 conjugated MANP and tfMANP (FIG. 5). A large amount of Cy5.5 conjugated tfMANP fluorescence was observed cytoplasm or vicinity of microglia and astrocytes of hippocampus and thalamus of rat bTBI model, which was significantly higher than in rats treated with the non-targeted Cy5.5 conjugated MANP (FIG. 8D). These results demonstrated that MANP and tf-MANP could effectively mediate the brain targeting of nanoparticles and had potential for brain drug delivery.

In case of the present studies targeted nano construct MANP, tf was possibly recognized as an endogenous unit and this enabled it to achieve higher concentrations inside the brain for a relatively prolonged period. Interestingly it was observed that lower distribution of nanoparticles in liver. Nanoparticles with nearly neutral and negative surface charges reported to reduce the adsorption of serum proteins, resulting in longer circulation half-lives. Kataoka et al., reported that neutral and anionic nanoparticles tend to long circulate and subsequently lower accumulation in livers and spleen. Positively charged nanoparticles, have a higher rate of nonspecific uptake in the majority of cells.

In the present study, evaluated were short term memory loss in acute and chronic time points for the following groups: control, blast, minocycline, tMANP, and MANP.

Figures 9A, 9B:
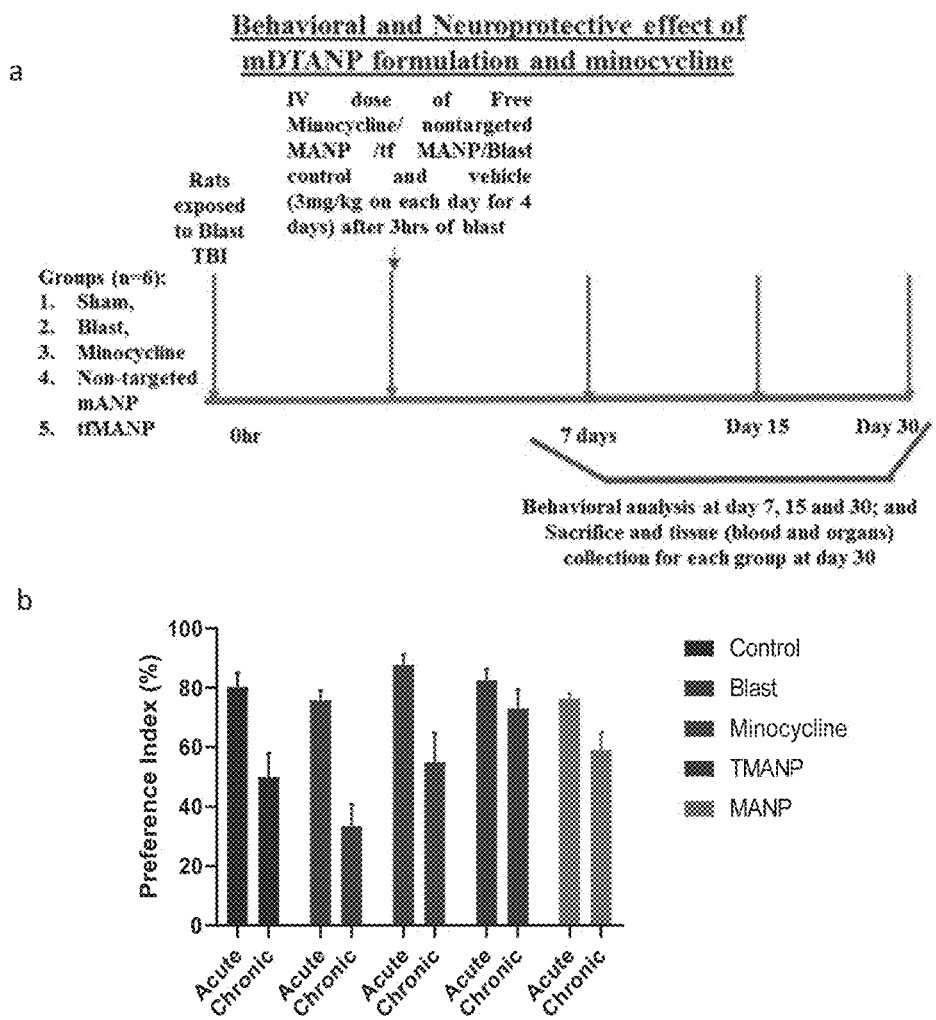
FIG. 9A-9B FIG. 9A (a) is a Schematic of Behavioral and Neuroprotective study.

In the present study and observation, blast group manisfetsted chronic short term memory loss whereas, miocycline treated group showed better performance in acute period. But, the effect of minocycline decreased over the time. Interestingly, both nanoparticle treated group of animals performed better at both acute and chronic time points (FIG. 9B).

Furthermore, in this present study, analyzed was anxiety between blast and the treated groups at acute and chronic time points. In this study it was observed that the tMANP treated animals explored open field arena (center zone) compared to any other treated and blast groups (FIG. 10).

Figures 11A, 11B:
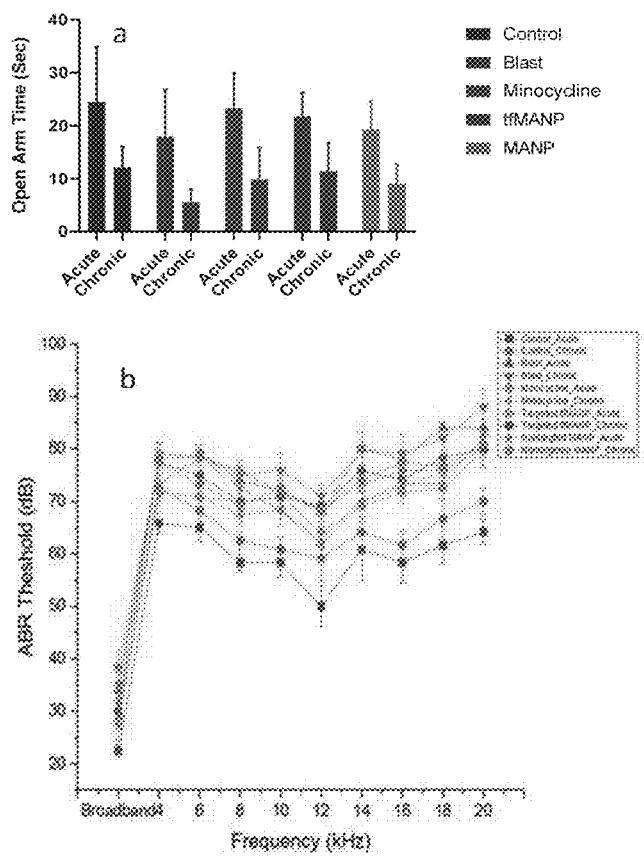
FIGS. 11A-11B were FIG. 11A (a) is a bar graph showing elevated plus maze for minocycline, tMANP and MANP treated moderate bTBI rat model (n=5)

Also in this present study, it was evaluated anxiety like symptoms in control, blast, minocycline, tMANP and MANP groups at acute and chronic time points. tMANP treated group of animals spent more time in open arm compared to all other treated groups (FIG. 11A).

Attenuation of bTBI-Induced Hearing Loss Using Minocycline, Non-Targeted MANP and Targeted tfMANP In the broadband, blast acutely caused significant increase of ABR threshold. While all three treatments on average reduced the ABR threshold individually. Minocycline free drug has the significant effect of reducing the ABR threshold compared with other two treatments (blast vs mino, p=0.022047, blast vs targeted, p=0.1572, blast vs non-targeted, p=0.8914). In chronic situation, minocycline free drug also showed the promising reduction effect on ABR threshold (FIG. 11A).

In the individual pitched tone ABR, at 6 kHz, 8 kHz, 16 kHz, 18 kHz and 20 kHz, blast caused acute ABR threshold increase. Whereas the increased threshold persisted at 6, 8 and 20 kHz in the chronic condition. With respect to the drug treatments, at 6 kHz, minocycline free drug in the chronic condition showed significant recovery compared with blast chronic condition. At 16 kHz, in both acute and chronic conditions, all three drug treatments had no significant effect on ABR threshold recovery. At 18 kHz, both minocycline free drug (blast vs mino, p=0.00333) and non-targeted nanoparticle treatments (blast vs non-targeted, p=4.9e-5) significantly reversed the ABR threshold increase caused by blast in the acute condition (FIG. 11A).

The results show that the nanoparticle designed to be delivered to brain have not reduced bTBI induced hearing loss compared to minocycline and non-targeted nanoparticle. This is possibly due to maximal delivery of targeted nanoparticle in brain and less therapeutic concentration of minocycline at cochlea and tympanic membrane. However, free minocycline showed significant recovery in hearing loss in acute and chronic timepoints compared to nontargeted nanoparticle.

Figures 17A, 17B:
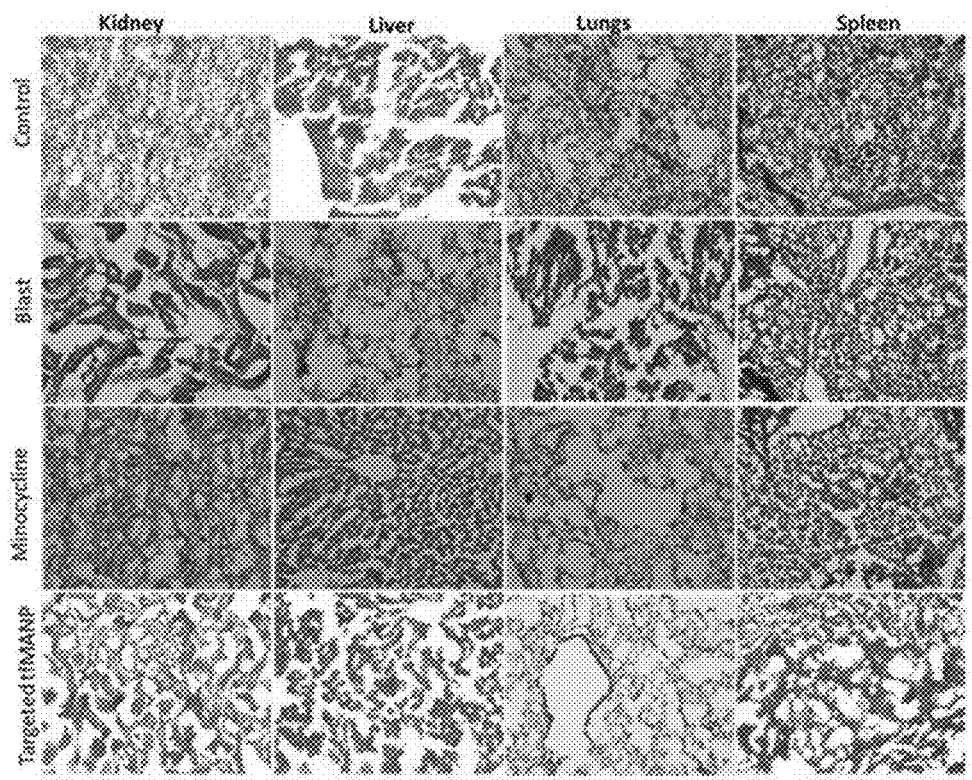
FIG. 17A-17B were
Figures 18A, 18B, 18C, 18D, 18E:
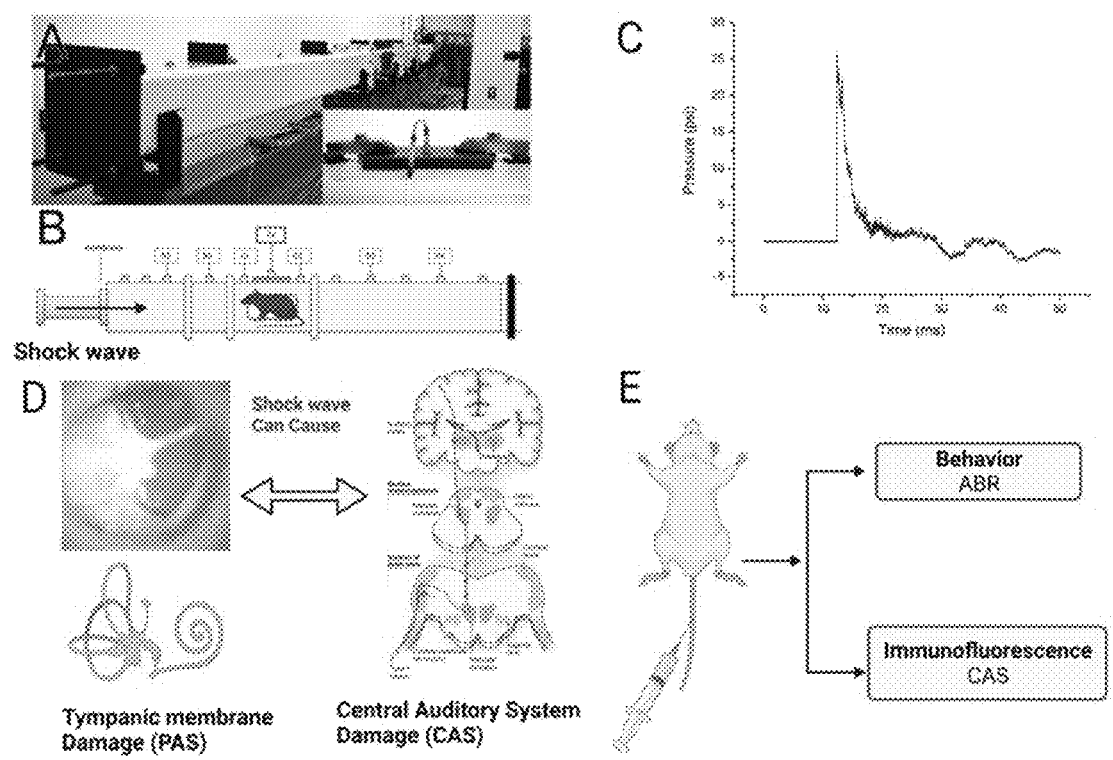
FIGS. 18A-18E are schematic photographs and figures illustrating in FIG. 18A is a photograph of the 9-inch square cross section, 22 ft long shock tube instrumented with pressure sensors.

FIG. 17A-17B show (a) histopathological evaluation of the major organs of rats treated with physiological saline, minocycline, non-targeted MANP and targeted tfMANP; histological analysis of the organs (liver, kidneys, lungs, and spleen) compared to the control group; no abnormal histopathological findings were observed in liver, kidneys, lungs, and spleen; (b) Body weight changes in blast TBI rats treated with physiological saline, blast, minocycline, non-targeted MANP and targeted tfMANP. Values are mean±SD (n=3) and have been analyzed using one-way ANOVA; data revealed significant ***p<0.001; after 15 and 45 days increase in the body weight in all treated groups as compared to the control group.

Body Weight Examinations

It should not induce overt toxicity or 10% or greater retardation of body weight gain as compared with control animals. Before treatment, body weight was determined for all the animals. As compared to saline treated control group, treatment with minocycline, non-targeted MANP and targeted tfMANP injection showed no reduction in body weight of Wistar rats. On the contrary all the treated groups increased the body weight similar to control groups (FIG. 17B). Taken together, repeated administration of minocycline, non-targeted MANP and targeted tfMANP did not cause any apparent toxicity. Further, no significant toxic effects were observed at all the injected doses.

Toxicity of Minocycline and Nanoparticle

The groups treated with minocycline, non-targeted MANP and targeted tfMANP exhibited mild changes in a few behavioral parameters, i.e., alertness and visual placing, passivity, spontaneous motor activity and touch response. No significant change in general signs was observed for any treatment group. Compared to untreated control/blast groups (transverse section of liver, lungs, kidneys, and spleen), no abnormal histopathological changes or lesions were observed in the minocycline, non-targeted MANP and targeted tfMANP treated groups (FIG. 17A). Further, there was no neutrophil or monocyte/macrophage infiltration in the liver, kidney, lung, and spleen (FIG. 17A). H&E staining demonstrates no architectural changes in the liver, kidney, lung, or spleen with injection of the minocycline, non-targeted MANP and targeted tfMANP (FIG. 17A). At some places, the nuclear chromatin showed the irreversible condensation of chromatin in the nucleus of a cell undergoing pyknosis.

Nuclear chromatin stained darkly when stained for histological evaluation and thus revealed hyper-chromasia. Mild or negligible liver pathologies relating to minocycline, non-targeted MANP and targeted tfMANP injection included clusters of infiltrating cells that were sporadically found in the liver, and suspicious necrotic hepatic cells however, none of these changes were significant.

The targeted albumin nanoparticle of minocycline and loaded targeted nanoparticle provides enhanced brain delivery and subsequent therapeutic application in moderate blast TBI model and is shown in this novel study (as indicated in previous FIG. 1 schematic). Nanoparticle administered at minimal dose in rat blast TBI model, exhibited the BBB crossing and enhanced therapeutic concentration compared to free minocycline.

It was also reported that the formulation of minocycline nanoparticles resulted in decreased accumulation of drug in liver, spleen, kidney and heart. Because of formulation of Minocycline as nanoparticles, a decreased accumulation in liver, spleen, kidney and heart resulted in lowering of toxic effects of minocycline in these tissues. This concentration achieved at those tissues were unable to produce any adverse effect on brain tissue. Reduced uptake of the PEGylated nanoparticles may reduce the toxicity of drug. Further theses nanoparticles were designed to be targeted delivered to brain endothelial cells. Hence, the treatment of non-targeted MANP and targeted tfMANP considerably reduced the hematological adverse effects of pure minocycline.

Again, to the best of the present investigator's knowledge, there has been no report on formulation, characterization and therapeutic effect of minocycline loaded albumin nanoparticles in moderate bTBI model. Therapeutic effect of free minocycline was also not explored in moderate bTBI model.

Further, the same nanoparticle structure can also be applied in other neurological conditions including traumatic brain injury, Parkinson diseases, Alzheimer disease, brain HIV, cancer, and other brain injuries, and blast hearing loss. A further description of therapeutic treatment using the methods and compositions discussed herein for blast hearing loss shall now be discussed.

Drug delivery to brain is limited by blood brain barrier (BBB). Similarly, blood labyrinthine barrier (BLB) plays a crucial role in separating and maintaining the unique fluid composition within the cochlea. Nevertheless, the precise anatomic location of the BLB is not well characterized in the cochlea. Multiple barriers between the inner-ear fluid lumen and vascular capillaries limit the rapid access of most compounds and therapeutic drugs to the cochlea. Therefore, drug delivery to the brain and inner ear faces many challenges. Owing to limitations of traditional drug administration and the specific structure of the inner ear, it is critical to explore novel, effective administration methods for hearing loss.

Stealth nanoparticles, depending on the embodiment includes polylactic acid (PLA) coated with polyethylene glycol (PEG), have been developed as a promising new avenue for delivering compounds to the cochleae in a sustained and controllable manner owing to the restricted diffusion of drug molecules and the controlled degradation of nanoparticles. Previously, it was found that dexamethasone encapsulated in PEG-coated PLA nanoparticles locally applied onto the round window membrane (RWM) of guinea pigs could maintain the concentration of DEX in perilymph at desired levels for a long period of time resulting in significant protection against cisplatin ototoxicity. Nanoparticle (NP)-based drugs have shown benefits of stable controlled release and functional surface modification, and NP-based delivery systems have become a research hotspot.

For the systemic delivery, high doses of drugs are required to targeted areas of poor blood circulation, such as the inner ear, which however, leads to unexpected severe adverse effects in other parts of the body. Therefore, new strategies to the delivery of therapeutic molecules to the inner ear are highly demanded. Owing to limitations of traditional drug administration and the specific structure of the inner ear, it is critical to explore novel, effective administration methods for the inner ear.

Even though minocycline crosses BBB, achieving therapeutic concentration to elicit an effect is challenging and limiting its use in various brain related diseases. In particular, to understand the CAS based mechanism of mitigating drug/noised induced hearing loss, there is great demand for targeted delivery approach of therapeutics including minocycline via BBB. Therefore, new strategies to the delivery of therapeutic molecules across these barriers for hearing loss are highly demanded.

Previously analyzed was the transduction efficacy of Cy3-labeled silica nanoparticles to central auditory nervous system. The distal part of the central auditory pathway (dorsal cochlear nucleus, superior olivary complex) was found to be labeled with the Cy3-linked silica nanoparticles, indicating a retrograde axonal transport. In particular, albumin-based nanoparticle has been explored widely for the effective delivery of therapeutics to cancer, brain disorders. Therefore, a therapeutic regimen is desirable that is able to ameliorate auditory damage when administered after a blast exposure has occurred.

Accordingly, the present investigators conceived that minocycline, BBB targeted transferrin tagged and PEGylated (non-targeted) formulation should facilitate sustained release of the drug after systemic (i.v) administration, leading to a protection against bTBI induced hearing loss through peripheral and central mechanism. In the present study, systemically administered was minocycline, BBB targeted transferrin tagged and PEGylated (non-targeted) formulation to bTBI induced hearing loss in rats, and examined the function and histology of the rats cochleae to evaluate their potential protective effect against bTBI induced hearing loss.

The purpose of the below described study for blast hearing loss was to determine if administration of a minocycline and its targeted and non-targeted nano-formulation with four days of consecutive injection after blast exposure could reduce both acute and chronic hearing loss through peripheral and central mechanism. To this end, a blast was developed, and the operational conditions established for exposing rats to moderate pressure comparable to those encountered in an open-field blast of single 26 pounds per square inch (psi) (180 kPa). This blast model produced reproducible blast overpressures that resulted in physiological and physical damage to the auditory system that was proportional to the number and amplitude of the blasts.

The present investigators are not aware of any other attempt to evaluate whether minocycline and the presently disclosed nano formulation has for otoprotective effects in moderate blast induced hearing loss rat model through peripheral and central mechanism.

Materials Methods
Chemicals, Reagents, and Instruments

Minocycline, Bovine Serum Albumin (lyophilized powder, ≥96% agarose gel electrophoresis), anhydrous ethanol (200 proof, anhydrous, ≥99.5%) crosslinker NHS-PEG-MAL-5000 and transferrin (human: minimum 98%) were purchased from Sigma Aldrich U.S.A. HPLC Grade Ammonium acetate was purchased from VWR. HPLC grade water, Methanol and Acetonitrile were purchased from Fisher Scientific. HPLC-grade glutaraldehyde (100%) were obtained from Alfa Aesar (USA). The Millipore Milli-Q Plus apparatus was used to procure ultrapure water. All other chemicals used in this study were of analytical grade. Traut's reagent (2-Iminothiolane) and Ellman's reagent was obtained from Pierce (Rockford, USA). The PD-10 Columns Sephadex™ G-25 M were from GE Healthcare. Lyophilizer, Centrifuge (Eppendorf centrifuge 5810R, Thermo scientific Sorvall RC 6+), Zeta sizer (malvern), HPLC (Thermo Fischer), Sonicator and Rota evaporator (Rotaevapor Buchi, R-210) instruments were used in the study.

Test Subjects:

Utilized were 10-week-old adult male Sprague-Dawley (Charles River Laboratories) rats weighing 250±50 grams were used in this study. The animals were housed with free access to food and water in a 12-h dark-light cycle at constant monitoring at 25° C. All conducted experimental procedures followed the guidelines of Care and Use of Laboratory Animals approved by Rutgers University Institutional Animal Care and Use Committee before experiments. Rats were divided into five groups: 1) Control, 2) Blast, 3) Blast+Minocycline injection 4) Blast+BBB targeted transferrin tagged nanoparticles and 5) Blast+and PEGylated (non-targeted) nanoparticles. Animals in the control group were placed outside of the shock tube exposed to only the sound (no shock wave). While animals in 180 kPa blast group, they were exposed to both sound and shock wave.

Blast Injury

Rats were exposed to a single moderate blast shock wave at the New Jersey Institute of Technology (Center for Injury Biomechanics, Materials, and Medicine) in the shock tube. 180 kPa was chosen as the non-severe blast overpressure level in this study. Prior to blast exposure, all animals were anesthetized with 5% isoflurane, released in a chamber containing 95% air and 5% $CO_2$, until rats were unresponsive to paw and tail pitch. Then animals in blast group were fastened on the stage facing the direction of the blast wave as illustrated in FIG. 1(i). The control group was placed outside of the shock tube to avoid shock wave, only the blast sound was exposed as shown in FIGS. 18A-18E, and specifically in FIG. 18B.

Blast Overpressure Measurement

The real time pressure was recorded along the shock tube. The position of the pressure sensors is listed in FIG. 18A-18E as B1, C1, T4, C2, D2 and D4. Typical 180 kPa blast profile with all six pressure sensors recordings is displayed in Figure, the T4 sensor recorded what the animal was experiencing during the blast. The sensor displayed the typical overpressure-under pressure profile, and the shock tube generated 180 kPa (~26.107 psi) in peak pressure and within a millisecond time duration.

Preparation of BBB Targeted Transferrin Tagged and PEGylated (Non-Targeted) Minocycline Loaded Nanoparticles Again, BBB targeted transferrin tagged nanoparticle was formulated in three steps. In the first step, minocycline encapsulated albumin nanoparticle was prepared using a modified desolvation method. Briefly, 10% BSA (w/v) in HPLC grade water was stirred (at 600 rpm) with 7.5% of minocycline (w/v) at room temperature for drug absorption onto albumin. After 1 h of continuous stirring, the pH value was adjusted from 8.5 using 0.1 M NaOH. The mixture was then desolvated through addition of a suitable amount of ethanol, using a peristaltic pump at a rate of 1 ml/min under stirring (at 600 rpm). Ethanol addition was sustained till turbidity point and residual ethanol was removed by a rotary evaporator at 4° C. Then, the formulated minocycline-loaded nanoparticle was stabilized by crosslinking with 8% glutaraldehyde solution for 18 hr. The nanoparticle in solution was ultra-centrifuged (Sorvall LYNX 6000, Superspeed Centrifuges) at 36288 g force for 40 min.

In the second step, 2-iminothiolane solution was added to bind a sulfhydryl group to the transferrin, and was quantified through use of Ellman's reagent. Briefly, transferrin was dissolved in phosphate buffer (1 mg/ml at pH 8.0) and incubated with 12.8 µl (50.85-fold molar excess) of 2-iminothiolane solution (6.9 mg in 1.0 ml phosphate buffer, pH 8.0) in the dark for 2 h at 20° C. under constant shaking (500 rpm). Thereafter, the thiolated transferrin was purified by PD-10 Columns Sephadex™ G-25 M, using phosphate buffer (pH 8.0) as eluent.

In the third step, NHS-PEG-MAL-5000 solution in 10-fold molar excess was introduced to the nanoparticles to cross-link activate them. To conjugate the NPs, 500 µl of thiolated and purified transferrin solution was added to 500 µl of reactive BSA NPs. The mixture was incubated under shaking for 24 h at room temperature. Thiolated transferrin excess was removed by 2-fold nanoparticle centrifugation, redispersed in water and lyophilized. Precipitate obtained from the centrifugation was washed with pure water three times and then freeze dried with addition of 50 mg mannitol to obtain brownish fine powder of Tf conjugated MANP. For further characterization, a stock suspension of NP was used. Similarly, non-targeted nanoparticle was also prepared without the transferrin ligand conjugation.

Two separate approaches were utilized to redisperse the lyophilized MANP, physical shaking and sonication. Manually shaking method was applied using weighed quantity of lyophilized NP with phosphate buffer saline pH 7.4. The nanosuspension was subject to gentle shaking for 2 min to redisperse the solution and then immediately measured for particle size using a Malvern zetasizer. After gentle shaking for 2 min, the nanosuspension was subjected to particle size measurement using Malvern zetasizer. Micrometer sized particles were considered too non-dispersible. Sonication method was applied with lyophilized NP in phosphate buffer saline pH 7.4 for 2 min using a bath sonicator and redispersibility.

Drug Administration

Animal test subjects in the treated group were tail vein injected intravenously (i.v.) with a 3 mg/kg minocycline, BBB targeted transferrin tagged and PEGylated (non-targeted), which were dispersed in 0.5 ml of physiological saline solution. Drug administration was started 4 h after blast overexposure and then continued once a day for the following three days. Animals in the control group were injected i.v. with a similar volume of saline according to the same schedule as the treated group.

Auditory Brainstem Response (ABR)

Cochlea conditions and inferior colliculus integrity were examined by ABR at post day 7 and 30 in control, blast, minocycline, BBB targeted transferrin tagged and PEGylated (non-targeted) nanoparticle group. ABR thresholds were recorded as the parameter of functional evaluation of neuronal circuit between cochlea and inferior colliculus. For each above-mentioned time points, animals were examined for tympanic membrane (TM) rupture conditions by using otoscope. After the blast exposure, when animals were still under the effect of anesthesia, a commercialized Teslong Ultra-Thin Otoscope (3.9 vmm HD Visual Ear Cleaner Ear Scope Camera with six LED Lights) were inserted in the pre-cleaned (with Q tips and alcohol) ear canal of the animals. Animals were placed on the heating pad to avoid hypothermia. The ear tip was used for the guidance of the otoscope camera. Tympanic membrane (TM) pictures were taken when the camera was capturing the most range of the tympanic membrane (TM). Animals were anesthetized with 5% isoflurane, released in a chamber containing 95% air and 5% $CO_2$ for one minute then placed on the heating pad when doing TM examination in other time points.

TM ruptured animals were excluded from the ABR examination. Then animals were initially anesthetized. Three platinum-coated tungsten electrodes were inserted in the vertex, below the ipsilateral pinna, and in the hind leg muscles for the positive, negative, and ground positions, respectively. Click and tone-burst stimuli at 4, 6, 8, 10, 12, 14, 16, 18, 20 kHz were delivered through TDT M1 for free field operation. Stimuli were played from 100 to 5 dB with 5 dB stepwise decrease. ABR signals were amplified, band-filtered from 0.3 to 3 kHz, notch-filtered at 60 Hz, and averaged 300 times for click and tone-burst stimuli, respectively. ABR threshold was defined as the lowest sound stimulus level at which ABR waves can be identified.

Immunohistochemistry and Microscopy

Rats were cardiac perfused with 4% Paraformaldehyde in 9.6 g/L PBS after injury. The heads of the animal were harvested, and the skin was removed to expose the dorsal surface of the skull. The cerebrum, cerebellum, and brain stem were exposed and harvested by breaking the occipital bone and parietal bone. The brain specimen then was fixed in 4% Paraformaldehyde in 9.6 g/L PBS for 2-4 days, rinsed in 9.6 g/L PBS and stored in 30% sucrose 9.6 g/L PBS solution. Brains were then dissected into 20-micron thickness sections using Rat Brain vibratome (Kent Scientific Corp.) and then mounted on glass slides. Auditory cortex (AC) and inferior colliculus (IC) were identified by referring to Rat Atlas.

Tissue sections (20 μm thick, freshly cut by vibratome) were fixed in ice-cold methanol (100%) solution for 10 minutes at −20° C., blocked in 10% donkey serum at room temperature for 1 hour in PBS containing 0.03% Triton X-100. Fixed tissues were incubated overnight at 4° C. with respective primary antibodies to NMDA-R1 (1:150, abcam68144), GABAAR alpha 1 (1:500, abcam33299), NeuN (1:200, abcam104224). NMDA-R1, GABAAR alpha 1 were double stained with NeuN respectively. IBA 1 (1:300, Invitrogen, PAS-18039) and GFAP (1:300, abcam53554) were single stained, respectively. Secondary antibodies conjugated with Alexa Fluor 594 (red) were used for both NMDAR, GABAA receptors and GFAP separately. Alexa Fluor 488 (green) were used for NeuN and IBA1. Antifading reagent with DAPI (ProLong™ Gold Antifade Mountant with DAPI, Invitrogen) was used before putting cover slide.

Image Acquisition and Quantification

Following immunostaining, after one night drying in the dark room, slides were digitized (20× magnification) using Leica Aperio Versa 200 fluorescent microscope and slide scanner. Fluorescence intensities in the above mentioned three regions was quantitated using Area Quant software (Leica Biosystems) and expressed as average fluorescence intensity/unit area.

Results and Discussion

Although many NP-based drug-delivery systems have been discovered to date, those that have received FDA approval for clinical use are few and have shortcomings. The present investigators have developed a NP-based drug-delivery system, composition and delivery method that demonstrated promising prospects for clinical targeted treatment of hearing loss.

Passive and active methods for local delivery can be categorized into two general groups: intratympanic or intracochlear. The intratympanic approach is a non-invasive method that preserves hearing and takes advantage of the permeability of the round window to gain access to the cochlea. However, this technique is limited by not knowing the dose of the drug that reaches the cochlea, (a handicap which might be overcome by the use of tagged drugs). Cyclodextrin, a common drug carrier, solubilizes the plasma membrane by releasing glycosylphosphatidylinositol-anchored proteins and sphingolipid domains. Cyclodextrin entry into the inner ear environment may be possible by perforating the BLB. When used in this manner, high doses of cyclodextrin are toxic to outer hair cells, causing moderate to severe hearing loss. While some systemic treatments exist, they generally exert adverse secondary effects and their efficacy is hampered by the blood-cochlear barrier that limits drug access to the inner ear. Hence, further the need for the disclosed new therapies for hearing loss and strategies for direct drug delivery to the inner ear.

Systemic drug delivery is considered as the first line approach as the treatment modality for inner ear disorders such as idiopathic sudden sensorineural hearing loss (ISSNHL) including noise-induced hearing loss, vertigo, and Meniere's disease. The main benefit associated with systemic drug delivery is the ease of administration especially when given orally in the form of pills. However, systemic drug delivery leads to undesirable side effects due to the inner ear's limited blood supply and the relatively poor penetration through BBB and blood-inner ear barrier (BLB). This leads to sub-therapeutic local concentration of the drug and the need for higher systemic doses in order to reach therapeutic range. It increases the numerous adverse side effects of systemically delivered drugs such as corticosteroids that are commonly used to treat inner ear conditions. The present investigators have shown that blast-induced traumatic brain injury is different from other forms of injury since supersonic shock waves accompany the blast that the wave is capable of penetrating the skin, skull, and the brain. The CAS dysfunction is likely mediated by direct transmission of shockwaves in all the regions of central nervous system (CNS), including nerves and surrounding tissues along the auditory pathways. The present investigators have also established that the shock wave and accompanying noise in the blast loading enter not only the outer, middle, and inner ears of the peripheral auditory system (PAS) but can directly damage the central auditory system (CAS), including the brainstem, thalamus, and auditory cortex. It is noteworthy that the central auditory damage observed in the present study could be direct mechanical damage (caused by shock waves) to neuronal synapses in vulnerable brain regions, and definitive evidence of what secondary factors cause these changes is still unavailable. However, the present investigators believe that using rats exposed to moderate blast pressure (23 psi), overpressure displayed a significant increase in oxidative damage in several brain region that is comparable to that used in the current study. It is likely that secondary damaging factors that are elevated by direct mechanical injury to both peripheral and central auditory regions could evolve into central neurotransmitter changes which may ultimately contribute to permanent hearing loss in blast injury.

Generally, severe, and persistent post-injury central auditory processing (CAP) deficits were observed in blast-exposed animals throughout the auditory neuro-axis, spanning from the cochlea to the cortex. The present investigators have also shown that blast increases blood-brain barrier permeability and activates microglial immune response. These changes could impact on the neurotransmitter receptor. These direct biochemical changes are likely to affect the entire central auditory pathways including the brainstem, midbrain, and auditory cortex. Thus, the present investigator's work reiterates that that blast can cause central damage (including auditory pathways) through direct transmission in addition to the damage to the peripheral system due to high pressure waves interacting with the external meatus of the ear canal. In CNS, blast exposure significantly alters the levels of various neurotransmitter receptors including glutamate GABA, serotonin, and acetylcholine, which contribute to central auditory damage. The major focus of the study is to provide the needed bioavailability/cell targeting in the injured brain at a significantly lower dose to achieve maximum bioavailability of minocycline through a targeted nanoparticle and subsequent effect on hearing loss.

The presently proposed research of (BBB) targeted transferrin tagged (tfr-transferrin receptor) and PEGylated (non-targeted) minocycline entrapped albumin nanoparticle was found to deliver the minocycline to brain in mitigating the blast/noise induced hearing loss in rat model through CAS mediated effect.

In the present study, albumin protein-based NPs was obtained by a process of desolvation that can be achieved through precise addition of desolvating agent (ethanol) to albumin solution at an optimum pH (optimal size and encapsulation) with constant stirring until turbidity. A decrease in the solubility of albumin followed by phase separation in water during the desolvation process leads to nanoparticle formation. Further the nanoparticles can be stabilized by crosslinking lysine and guanidino side chains of albumin with the crosslinking agent glutaraldehyde. When crosslinking is increased, the rigidity of the nanoparticle can lead to successive decreases in particle size due to the formation of more compact particles. In our study, hydrophobic minocycline aggregates in aqueous solution and interacts with the hydrophobic regions of the BSA forming nanoparticle, which was stabilized with glutaraldehyde by cross-linking the surface amino groups of BSA. The $NH_2$ from BSA molecule when comes in contact with the carbonyl group of glutaraldehyde, reacts to form the —N=C— bond by losing a molecule of water. In this way the nanoparticles of albumin crosslinked with glutaraldehyde are formed. The glutaraldehyde crosslinked with albumin has no toxicity, and the obtained NPs are non-toxic. However, the free unbound glutaraldehyde may display toxicity. Hence, unreacted glutaraldehyde was removed by centrifugation and purification.

Minocycline-loaded albumin nanoparticles (both BLB/BBB targeted and PEGylated) were freeze dried with 0.05% of mannitol, resulting in a brownish powder that can also be dispersed in PBS or 0.9% saline solution. Nanoparticles with uniform size allow increased cellular interaction and possess enhanced toxicity. Lyophilization may increase the particle size of the nanoparticle, possibly due to aggregation; hence we checked the redispersibility of the particles after lyophilization using mechanical shaking and bath sonication methods.

Figures 19A, 19B:
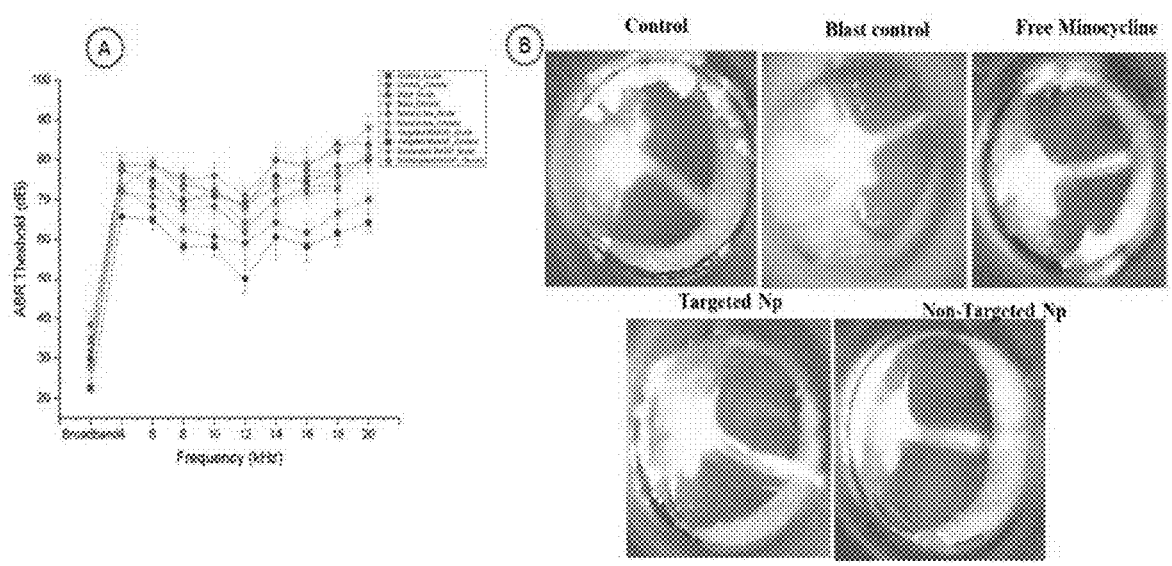
FIGS. 19A-19B are a graph and photomicrographic images illustrating in FIG. 19A mean ABR thresholds and shifts after blast TBI in rat model at acute and chronic conditions; the rats were treated with sham, blast, minocycline, non-targeted MANP and targeted tfMANP group; error bars represent SEMs. *P<0.05.

Minocycline, BBB Targeted Transferrin Tagged and PEGylated (Non-Targeted) Minocycline Nanoparticles on Auditory Brainstem Response (ABR):

As shown in FIGS. 19A-19B, the tympanic membrane was intact before the ABR examination. Also shown in these figures, in acute condition, the blast treated animal displayed significant increase in ABR threshold. However, the 3 different drug treatments shown in the figures have groups on an average reduced the ABR threshold level.

Unexpectedly, the free minocycline drug has the significant effect of reducing the ABR threshold compared with other two nanoparticle treatments (ANOVA post hoc, compare Blast exposed group with free minocycline treated group, P value=0.02205; compare Blast exposed group with BBB targeted transferrin tagged nanoparticles treated group, P value=0.1572, compare Blast exposed group with non-targeted nanoparticles treated group, P=0.8914).

In chronic condition minocycline free drug also showed the promising reduction effect on ABR threshold. In the individual pitched tone ABR at 6 kHz, 8 kHz, 16 kHz, 18 kHz and 20 kHz, blast caused increase ABR threshold in acute level, whereas the increased threshold persisted at 6, 8 and 20 kHz in the chronic condition. While with the minocycline drug treatments showed significant recovery compared with acute condition at 6 kHz, in the chronic condition At 16 kHz, in both acute and chronic conditions, all three drug treatments had no significant effect on ABR threshold recovery. At 18 kHz, both minocycline free drug (compare Blast exposed group with free minocycline treated group P value=0.00333) and PEGylated non-targeted treatments (compare Blast exposed group with non-targeted treated group, P value=4.9e-5) significantly reversed the increase in ABR threshold caused by blast in the acute condition.

The results show that the nanoparticle designed to be delivered to the brain have not reduced blast induced hearing loss compared to minocycline and PEGylated (non-targeted) nanoparticle. This is possibly due to maximal delivery of BBB targeted transferrin tagged nanoparticle in brain which in turn resulted in less effect on auditory brain response. However, free minocycline shows significant recovery in hearing loss both in acute and chronic timepoints compared to PEGylated (non-targeted) nanoparticle.

The present investigators previously discovered that minocycline ameliorates cochlear damage caused by intratympanic injection of the ototoxic aminoglycoside antibiotic neomycin in gerbils. After receiving 40 mM intratympanic neomycin with 1.2 mg/kg and 1.5 mg/kg, there were significantly lower ABR threshold increases compared to vehicle, especially in 6 kHz and 19 kHz. It was also revealed that minocycline treatment enhanced survival of spiral ganglion neurons and hairs cells. Not only for chemical induced hearing loss, noise-induced hearing loss (NIHL) was also alleviated by intraperitoneal administration of minocycline (45 mg/kg/d) for 5 consecutive days shown in ABR threshold study.

Minocycline treatment can also reduce noisy environment induces neuroinflammation. In the present study, administered were all 3 formulations via intravenous route with reduced dose and exhibited exception results. There was also minocycline nanoparticles usage for neuronal implants in order to quench the adverse inflammation. It was found that minocycline-loaded PLGA nanoparticles from gelatin-coated neural implants reduces brain tissue adverse inflammation and rejection responses in mice. This nanoparticle significantly reduced the activation of microglial cells and the astrocytic response. PEG-PLA NPs can be used to encapsulate dexamethasone (DEX) for intratympanic preconditioning of guinea pigs, and cisplatin was used to reduce the hearing of test subject animals. Administration of DEX-loaded NPs protected auditory function at 4 and 8 kHz, demonstrated that 6a-methylprednisolone loaded NPs protected auditory functions at 10, 14 and 16 kHz.

Reduction of Microglia and Astrocytes Activation in Both AC and IC

Figures 20A, 20B:
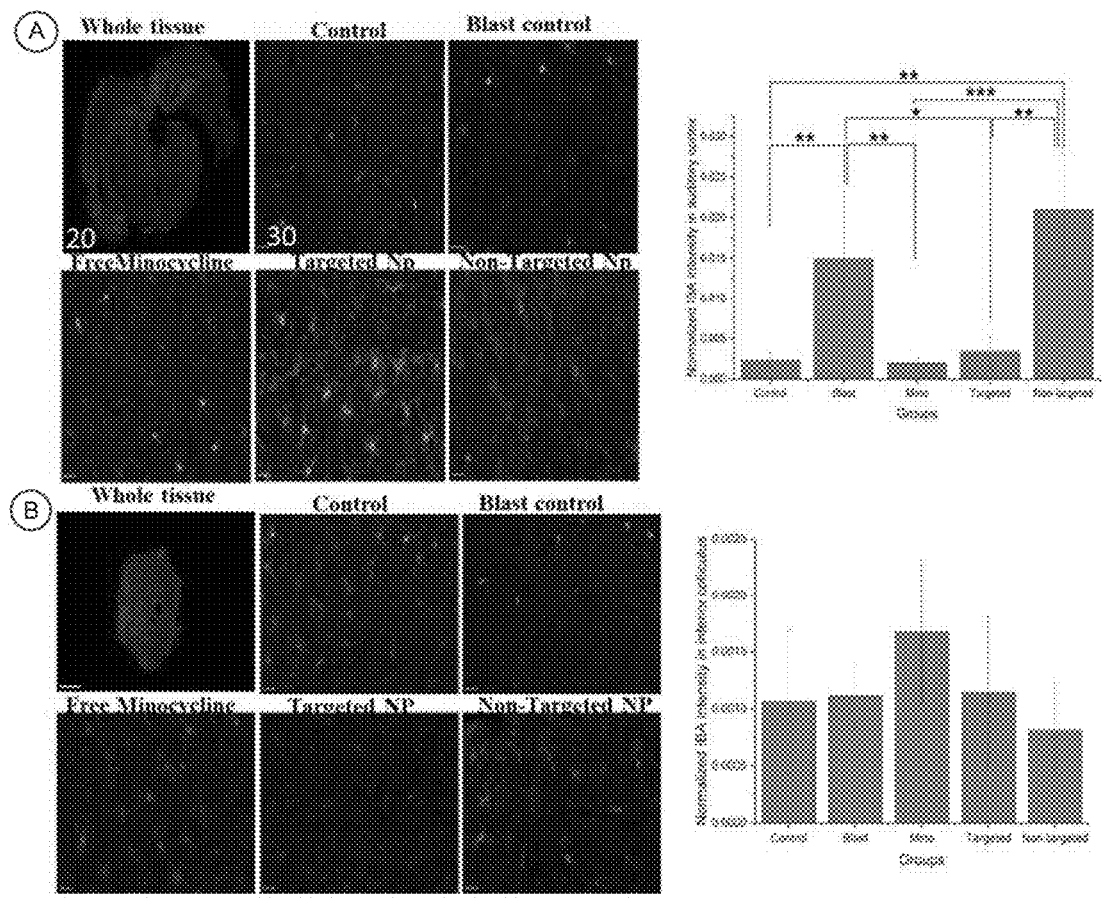
FIGS. 20A-20B are photomicrographic stained images and bar graphs illustrating fluorescence of IBA stained brain sections harvested from post-bTBI induced hearing loss rat model. Quantification of fluorescence intensities of IBA in different brain regions

In FIGS. 20A-20B, the IBA immunohistochemistry staining intensity is displayed. The graphs in the above figures revealed that after blast trauma, the intensity of microglia was elevated in AC which indicates the microglia activation in response to the blast induced tissue damages. After free drug minocycline and BBB targeted transferrin tagged minocycline nanoparticle treatment, the activated microglia level is significantly reduced. The group treated with PEGylated (non-targeted) nanoparticle treatment shows no change compared with that of the blast condition.

Blast group showed significant increase (p value=0.002) in microglial activation compared to control groups. Minocycline and targeted NP treatments show significant decrease (p value=0.003, and p value=0.03, respectively) compared to blast groups. Targeted treatment is still significantly different from the controls (p=0.000000783), suggesting no treatment efficacy. In Inferior colliculus, no significant change is occurred after the blast and all three treatments displayed the same intensity level indicating no significant activation of microglial level.

Figures 21A, 21B:
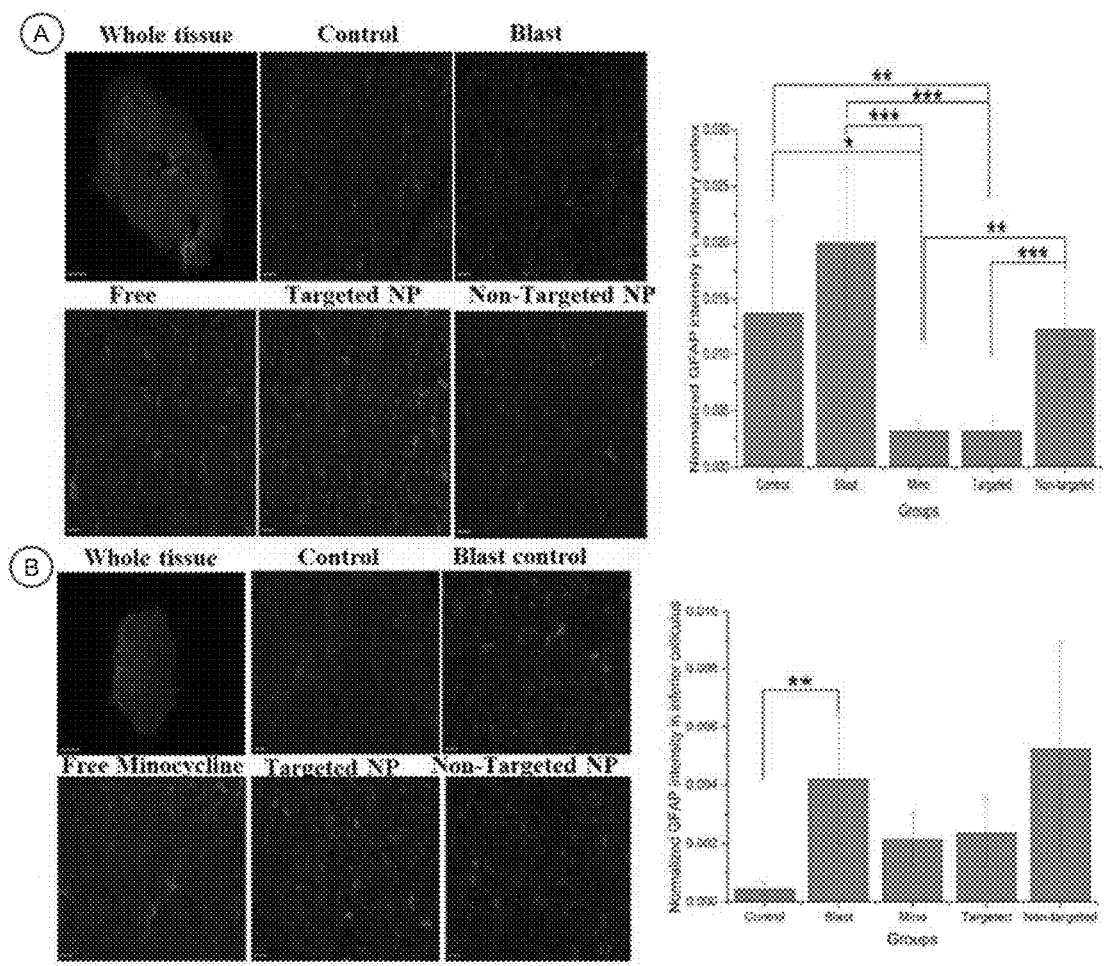
FIGS. 21A-21B are photomicrographic stained images and bar graphs illustrating fluorescence of GFAF stained brain sections harvested from post-bTBI induced hearing loss rat model. Quantification of fluorescence intensities of GFAF in different brain regions

In FIGS. 21A-21B, the GFAP immunostaining intensity with quantification among all five groups are displayed. The results in these figures show that after the blast trauma, the astrocytes level is elevated both in AC and IC. Both minocycline and targeted treatments are displaying promising recovery after blast injury except non-targeted treatment. In AC, compared with control, the blast group showed significant increase (P=0.005) in astrocytes level. All three treatment groups significantly reduced astrocytes level compared to blast group.

In inferior colliculus (IC), both minocycline (P value=0.01) and targeted nanoparticle (P value=0.001) treatment is showing decrease in astrocyte level compared to blast's level. Compared with blast, minocycline, and targeted nanoparticle treatment show significant decrease (P value=0.0000163 and P value=0.000000510, respectively) while the non-targeted nanoparticle treatment shows no significant change.

The present study shows that the minocycline nanoparticle and free minocycline treatment can reverse the increased in positive astrocytes and also microglia in AC. Similarly, it was previously revealed that minocycline has the inhibition effect on microglia activation. It was also showed in detail that minocycline treatment 24 h after moderate to severe controlled cortical impact injury (CCI) attenuates nuclear to cytosolic translocation of high mobility group box-1 (HMGB) in the post-natal day 17 Sprague-Dawley rats.

Minocycline treatment also reduced microglial activation in the ipsilateral cortex, hippocampus, and thalamus after 7 days. Another work studied the effect of minocycline on microglial/astrocytic activation in status epilepticus (SE) in lithium-pilocarpine-exposed rat hippocampi. It was found that microglia in CA1 and GFAP positive astrocytes in both CA1 and dentate gyrus (DG) were still higher in the SE with minocycline treatment group than in the control group. In addition, minocycline administration reversed the neuronal loss observed in DG. Concerning the blood-brain barrier (BBB), it is displayed that minocycline treatment prevented BBB permeability modulation and trigeminal sensitivity of chronic trigeminal allodynia in rat model. Not only for chemical induced hearing loss, noise-induced hearing loss (NIHL) is also alleviated by intraperitoneal administration of minocycline (45 mg/kg/d) for 5 consecutive days shown in ABR threshold study. Minocycline treatment can also reduce noisy environment induces neuroinflammation.

The present investigators found low dose of free minocycline and targeted or non-targeted nanoparticle administered via IV reduce the possibility of any toxicity associated with minocycline high dose treatment.

Recovery of Excitatory but not the Inhibitory Neurotransmitter Receptors

Mechanisms enabling trafficking of therapeutics across the BLB are conceptually similar to those for the BBB but require specialized adaptations specific to the cochlea and the vestibular system. Therapeutics could cross both the BBB and the BLB by diffusion through membranes if they are sufficiently lipophilic. The proportion of drugs with these physicochemical characteristics is estimated to be <1%.

For a small-molecule drug to cross the BBB, it must generally have fewer than eight hydrogen bonds and a molecular weight of <400 Da. Requirements for drug entry across the BLB are far less well characterized. The BLB and BBB can be opened by osmotic disruption using glycerin or mannitol; this has enabled delivery of antioxidants to the cochlea as oto-protectants during cisplatin chemotherapy in guinea pig models and in human patients. It was found out that claudin-1, claudin-3, and claudin-4 are expressed in marginal cells, and these cells form a barrier that separates intravascular fluid from the endothelium. Loss of macrophage-like melanocytes around the striatum capillaries can cause barrier damage and deafness. Noise exposure causes downregulation of occludin and claudin-5, resulting in increased BLB permeability. Increasing attention has thus been paid to the development of more effective treatments and efficient inner-ear drug-delivery systems. The main routes of systemic drug delivery include oral, intravenous, and intramuscular injections. Previous investigators confirmed that intravenous streptomycin can effectively control oto-genic vertigo. Otogenic (labyrinthine) vertigo is when the ear fails to keep individual's in equilibrium. Aminoglycoside antibiotics were later developed to treat Meniere's disease. Systemic steroids are widely used in the treatment of sudden sensorineural HL and autoimmune disease. Achieving the optimal concentration of systemic drugs in the inner ear is difficult because the BLB hinders their diffusion. Cellular processes could also transport therapeutics across the BLB, as occurs in the blood brain barrier (BBB).

These include specific and nonspecific endocytosis, as well as ion channels, ion exchangers, and transporters if the therapeutic is a bona fide substrate. Endocytosis includes the transcellular trafficking of cargo across the BLB endothelial cell barrier in either direction, which has been shown for cargo such as transferrin and amyloid-β. Aminoglycosides are ototoxic antibiotics that readily cross the stria and peri-lymphatic BLB through unidentified yet mechanisms, which are presumed to be intracellular transport processes due to saturable uptake kinetics.

Figures 22A, 22B:
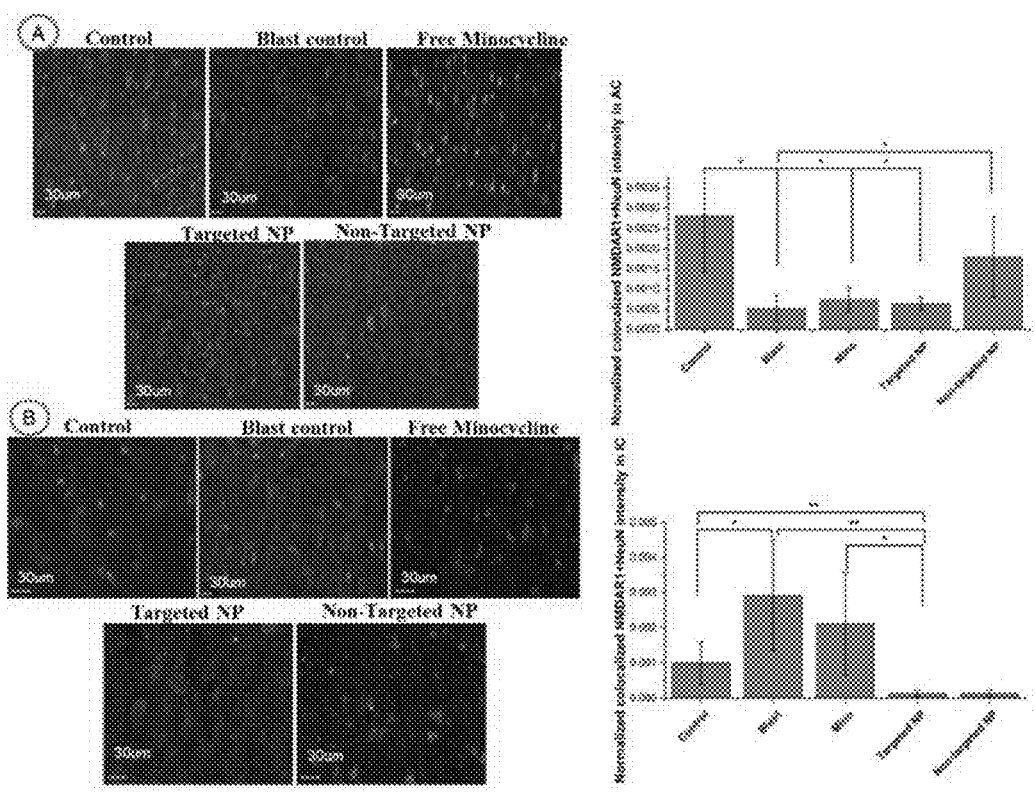
FIGS. 22A-22B are photomicrographic stained images and bar graphs illustrating fluorescence of NMDAR+NeuN stained brain sections harvested from post-bTBI induced hearing loss rat model; quantification of fluorescence intensities of NMDAR+NeuN in different brain regions

Adverting to FIGS. 22A-22B, shown is colocalization of NMDAR1 and NeuN intensity quantification. It shows that after the blast trauma, the intensity of the colocalization of NMDAR1 and NeuN intensity decreases in AC, while minocycline and targeted treatment have no effect on blast damage. In AC, blast caused significant decrease (P value=0.00707) in colocalization of NMDAR1 and NeuN intensity compared with control's, but both minocycline and targeted treatments also caused decrease compared with control's (P value=0.0304, P value=0.0318, respectively). While in non-targeted group, it shows significant increase compared with blast group (p=0.0397).

Interestingly, non-targeted treatment shows the better effect in comparison to other treated groups. This result is possibly due to the PEGylated stealth nanoparticle reaching the cochlea via compromised BLB. In one embodiment, stealth nanoparticle are made by encapsulating dexamethasone in PEG-coated PLA nanoparticles and injecting a single dose of stealth nanoparticle 1 hour before cisplatin administration. The results showed that, in contrast to free DEX, a single injection resulted in significant functional and histological protection of the cochlea from the cisplatin which was similar to the effect of repeated injection of free DEX for 3 days. The results suggested that it is likely due to the sustained delivery to the cochlea of high concentration of dexamethasone by using stealth-nanoparticle technology.

PLA (polylactic acid) nanoparticles with PEG coating efficiently escape from the mononuclear phagocyte system (MPS) in the liver and spleen resulting in prolonged circulation of PLA nanoparticles. Biocompatible and degradable biopolymers were initially investigated, and the surface modification of the NPs was shown to be effective for overcoming the barriers (epithelial membrane penetration and cellular uptake) to inner ear delivery.

Among other surface modifications, polyethylene glycol (PEG) coating, namely, PEGylation, is regarded as a promising method due to the increased diffusivity into cells or tissues. It was demonstrated that fluorescent dye-tagged NPs that were PEGylated exhibited significantly higher fluorescence levels in OHCs compared with those without PEGylation.

As an applicable example of drug delivery, PEG-coated polylactic acid (PEG-PLA) NPs loaded with dexamethasone were locally injected on the surface of the RWM33 to promote survival of the hair cells in the presence of cisplatin-induced ototoxicity and the maintenance of auditory function in guinea pigs. Previous investigators reported that free betamethasone phosphate (BP) disappeared from the cochlea within 12 h, while stealth-nano-BP could maintain higher BP concentrations in the cochlea for 24 h than were achieved after 1 h using free BP injections. This study supports the hypothesis that encapsulating therapeutic reagents in stealth nanoparticles is an effective strategy for sustained drug delivery to the cochlea via BLB. In IC, all three treatments revealed the positive effect of recovery after the blast. Targeted treatment displays significant decrease in colocalization of NMDAR1 and NeuN compared to control group's (P value=0.000761). Compared to blast, both targeted and non-targeted treatment displayed the significant decrease (P value=0.0000470, p value=0.0328, respectively) in colocalized intensity of NMDAR1 and NeuN. Moreover, the targeted treatment showed significant decrease in colocalization of NMDAR1 and NeuN compared to the minocycline treatment.

Figures 23A, 23B:
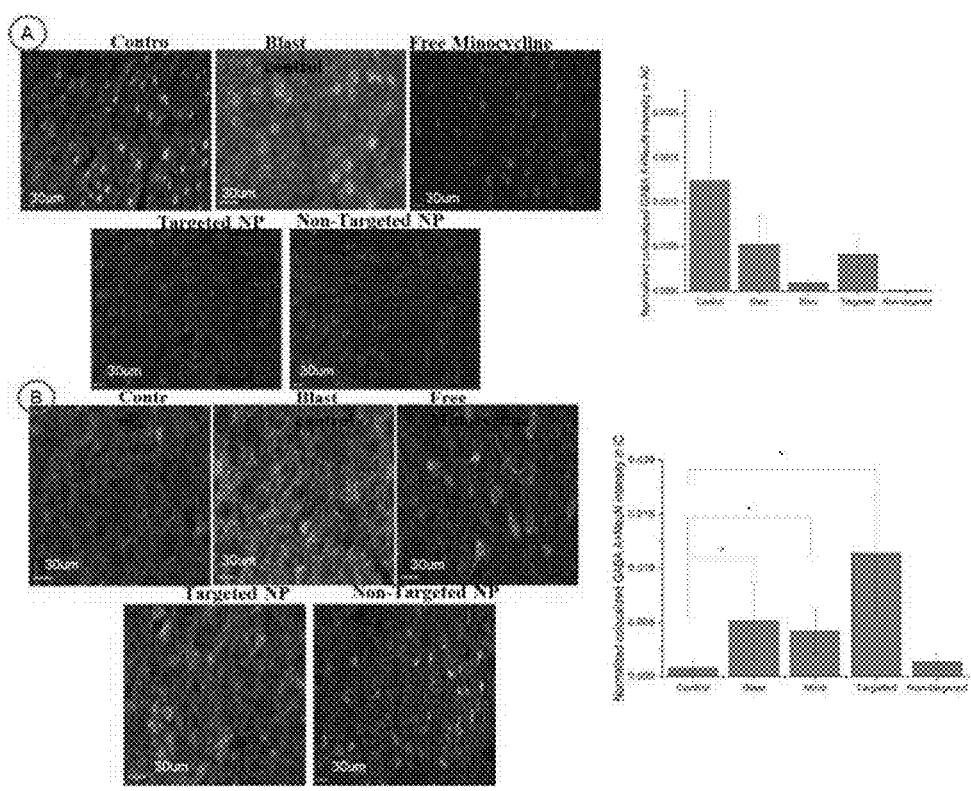
FIGS. 23A-23B are photomicrographic stained images and bar graphs illustrating fluorescence of GABA A+NeuN stained brain sections harvested from post-bTBI induced hearing loss rat model; quantification of fluorescence intensities of GABA A+NeuN in different brain regions

In FIGS. 23A-23B, displayed is the colocalization of GABAA and NeuN intensity quantification. It shows that in AC, there is no significant decrease after blast. Minocycline and targeted nanoparticle treated group are both showing significant decrease in colocalization of NMDAR1 and NeuN, revealing no effect of recovery (p=0.00740, and P=0.00855, respectively). Whereas in IC, it shows the intensity elevation after the blast (P=0.0427), and the non-targeted NP treatment shows no significant change in colocalization of NMDAR1 and NeuN compared with control's, indicating non targeted nanoparticle of minocycline reduces the blast induced NMDAR1 elevation.

The present investigators observed that minocycline also has seizure reduction and prevention effect. It was revealed that injection of minocycline in mice before seizure induction increased the latency to stage 4 seizure, and decreased the duration of stages 4 and 5 seizure. It maintains the mRNA of NR2A subunit of NMDA receptor and c2 subunit of GABAA receptor levels from being upregulated. It was extrapolated that minocycline may exert an anticonvulsant effect through preventing the increase in GABAA and NMDA receptor subunits. The present investigators previously showed that blast exposure reduces both NMDAR1 and GABAA receptor levels in acute condition (post-blast or Day 1) in AC and IC.

Clinically, the use of minocycline for hearing preservation would be limited by its partial efficacy, likely a reflection of redundant apoptosis pathways in hair cells and potential species differences. Several other agents that may partially protect hearing have been examined in animal models of chemical ototoxicity and noise mediated deafness. For example, the known free radical scavenger Allopurinol has been found to provide short term protection from hearing loss in guinea pigs.

Combination therapies including minocycline could potentially convey synergistic otoprotection in humans. Also, drug delivery approach, optimal dosages, and routes of administration, including i.v injection of nanoparticle formulation at reduced dose than toxic level. It was previously demonstrated minocycline protection effectiveness at 1.2 mg/kg. Dosages in other experimental models have demonstrated that efficacy of minocycline in terms of reduced cell death varies widely.

For example, in vitro, 0.1 µM minocycline has been shown to inhibit the apoptosis promoting enzyme activity of poly (ADP-ribose) polymerase 1 (PARP-1) and confer 85% increased survival of neurons in culture, and 5 mg/kg intraperitoneal minocycline delayed cell death and inhibited caspase-1 and caspase-3 expression in the brains of a mouse model of Huntington's disease. In humans 3-10 mg/kg intravascular doses of minocycline are being evaluated for use in stroke treatment. It should be kept in mind that some applications of minocycline that appear promising in animal models, for example, Huntington's disease, may not proceed to human use.

Despite the adverse effects, systemic drug delivery through oral, intravenous, or intramuscular methods are still accepted as the first line approach when treating inner ear disorders. It is believed that nanodrugs will ultimately provide the necessary solutions that will significantly enhance the field of drug delivery to brain to mitigate drug/nose induced hearing loss and will alter clinical practice in the future.

In summary, the present investigators developed a new drug delivery system for minocycline to improve the protective efficacy against blast induced hearing loss. It is assumed that the targeted nanoparticle cross BBB via transferrin receptor expressed in endothelial cells of BBB. In case of non-targeted PEGylated nanoparticles-coating the surface of nanoparticles with polyethylene glycol (PEG), or "PEGylation", is an approach for improving the efficiency of drug and gene delivery to target cells and tissues-reaches cochlea via the damaged/compromised BLB due to noise exposure and permeates free minocycline and nontargeted nanoparticles.

Although the invention herein has been described with reference to embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A targeted nanoparticle composition, comprising:
a minocycline loaded transferrin (tf) targeted albumin nanoparticle (tf conjugated MANP or tfMANP), the nanoparticle having:
   a bifunctional spacer crosslinker attached to the albumin nanoparticle;
   a sulfhydryl group attached to both the bifunctional spacer and the transferrin;
   wherein, the bifunctional spacer crosslinker is N-hydroxysuccinimide polyethylene glycol maleimide having a molecular weight 5,000 (NHS-PEG-MAL-5000), and the sulfhydryl group is 2-iminothiolane;
   the tfMANP having a particle size of 135.4 nm-153.5 nm, wherein the range of the particle size of the nanoparticle is for affecting cell interactions and toxicity;
   the nanoparticle further having an anionic surface charge of about −2.52 mV to −3.14 mV;
   wherein, brain bioavailability of minocycline for a single dose of the composition at a concentration of about 3 mg/kg lasts longer in a 24 hour period as compared to a conventional dosage of minocycline at about 20-100 mg/kg given at multiple doses per day.

2. The composition of claim 1, wherein the nanoparticle is further conjugated to a CD11b antibody.

3. The nanoparticle composition of claim 1, wherein the anionic surface charge is −3.14 mV.

4. The nanoparticle composition of claim 1, wherein the nanoparticle further includes a polydispersity index of 0.275±0.01.

5. A targeted nanoparticle composition, comprising:
a minocycline loaded transferrin (tf) targeted albumin nanoparticle (tf conjugated MANP or tfMANP), the nanoparticle having:
   a bifunctional spacer crosslinker attached to the albumin nanoparticle;
   a sulfhydryl group attached to both the bifunctional spacer and the transferrin;
   wherein, the bifunctional spacer crosslinker is N-hydroxysuccinimide polyethylene glycol maleimide having a molecular weight 5,000 (NHS-PEG-MAL-5000), and the sulfhydryl group is 2-iminothiolane;
   the tfMANP having a particle size of 135.4±5 nm, wherein the range of the particle size of the nanoparticle is for affecting cell interactions and toxicity;
   the nanoparticle having an anionic surface charge of about −2.52 mV to −3.14 mV;
   wherein, brain bioavailability of minocycline for a single dose of the composition at a concentration of about 3 mg/kg lasts longer in a 24 hour period as compared to a conventional dosage of minocycline at about 20-100 mg/kg given at multiple doses per day.

6. A method of formulating the minocycline loaded albumin based nanoparticle (tfMANP) of claim 1, comprising:
   preparing an unmodified minocycline loaded albumin nanoparticle (MANP) by a desolvation technique, wherein bovine serum albumin (BSA) is dissolved in a sodium chloride solution, incubated with minocycline and the pH adjusted for formation of nanoparticles;
   introducing a sulfhydryl group to a transferrin by reaction of amino groups with 2-iminothiolane; and
   activating the nanoparticles with a heterobifunctional crosslinker NHS-PEG-MAL-5000 using a 10-fold molar excess for a sulfhydryl-reactive transferrin to covalently couple to the nanoparticles to obtain a targeted MANP (tfMANP).

7. The method of claim 6, wherein preparing the unmodified MANP further includes:
   adjusting the pH to about pH 9 and the nanoparticles are formed by adding ethanol a peristaltic pump at 1 ml/min under stirring, and then crosslinking the nanoparticles with glutaraldehyde, purified by 3-fold centrifugation, and redispersed by ultrasonication.

8. The method of claim 6, wherein the activating the nanoparticles further includes:
tagging a second ligand that is a thiolated tf-transferrin to the nanoparticles by a conjugation method by adding the tfMANP to a thiolated tf-transferrin mixture, stirring, and washing by ultracentrifugation to obtain minocycline loaded albumin based nanoparticle (mDTANP).

9. A method of delivering a therapeutic composition for use in the treatment of traumatic brain injury, blast hearing loss, and central nervous system diseases, comprising:
   providing the composition of claim 1; and
   delivering the composition to an inner ear of a patient.

10. The method of delivering the therapeutic composition in claim 9, wherein the delivery of the minocycline is to the brain for mitigating a blast/noise induced hearing loss a central auditory system (CAS) mediated effect.

11. The method of delivering the therapeutic composition of claim 9, further comprising injecting through an intravenous injection a composition of PEGylated non-targeted minocycline to the inner ear of a patient.

* * * * *